United States Patent
Yang

(10) Patent No.: US 7,605,262 B2
(45) Date of Patent: Oct. 20, 2009

(54) PODOPHYLLOTOXIN DERIVATIVES

(75) Inventor: Li-Xi Yang, San Francisco, CA (US)

(73) Assignees: Sutter West Bay Hospitals, San Francisco, CA (US); Catholic Healthcare West, San Francisco, CA (US)

(*) Notice: Subject to any disclaimer, the term of this patent is extended or adjusted under 35 U.S.C. 154(b) by 0 days.

(21) Appl. No.: 12/016,926

(22) Filed: Jan. 18, 2008

(65) Prior Publication Data

US 2008/0113941 A1 May 15, 2008

Related U.S. Application Data

(62) Division of application No. 10/612,240, filed on Jul. 1, 2003, now Pat. No. 7,342,114.

(51) Int. Cl.
*C07D 519/04* (2006.01)
*C07D 307/00* (2006.01)
(52) U.S. Cl. .......................... 546/51; 549/299
(58) Field of Classification Search ................ 546/197, 546/51; 549/298, 299
See application file for complete search history.

(56) References Cited

U.S. PATENT DOCUMENTS

| | | | |
|---|---|---|---|
| 3,524,844 A | 8/1970 | Keller-Juslen | |
| 4,965,348 A | 10/1990 | Saulnier et al. | |
| 5,534,499 A | 7/1996 | Ansell | |
| 5,614,549 A * | 3/1997 | Greenwald et al. | 514/449 |
| 5,840,900 A | 11/1998 | Greenwald et al. | |
| 5,880,131 A | 3/1999 | Greenwald et al. | |
| 6,096,336 A | 8/2000 | Cao et al. | |
| 6,251,382 B1 | 9/2001 | Greenwald et al. | |
| 7,342,114 B2 * | 3/2008 | Yang | 546/197 |

FOREIGN PATENT DOCUMENTS

| | | | |
|---|---|---|---|
| FR | 2837824 A1 | | 3/2002 |
| GB | 1 114 123 | | 5/1968 |
| JP | 01117885 | * | 1/1989 |
| JP | 01 117885 | | 5/1989 |
| JP | 02300124 | | 2/1990 |
| WO | WO 96/23794 | | 8/1996 |
| WO | WO 98/07713 | | 2/1998 |
| WO | WO 0001417 | | 1/2000 |
| WO | WO 00/29427 | | 5/2000 |
| WO | WO 0029427 | | 5/2000 |
| WO | WO 0226220 | | 9/2001 |
| WO | WO 0202804 | | 6/2002 |
| WO | WO 02102805 | | 12/2002 |
| WO | WO 03/082875 | | 10/2003 |

OTHER PUBLICATIONS

Gupta et al. Anti-Cancer Drug Design (1987), 2(1), 13-23.*
Yang et al.STN Accession No. 2002:884382 Document No. 139:159531 Abstract of Lanzhou Daxue Xuebao, Ziran Kexueban (2002), 38(2), 101-105.*
Xiao et al. STN Accession No. 2002:306357; Document No. 137:56983, Abstract of Journal of Medicinal Chemistry (2002),45(11), 2294-2309.*
Thurston et al. Journal of Medicinal Chemistry (1989),32(3), 604-8.*
Levy et al. Journal of Pharmaceutical Sciences (1983),72(10), 1158-61.*
Greenwald et al.STN Accession No. 1999:568594; Document No. 132:15517, Abstract of Journal of Controlled Release (1999), 61(3), 281-294.*
Shi et al. Bioorganic and Medicinal Chemistry, 9 (2000), 2999-3004.*
Xiao, et al., "Antitumor Agents. 213. Modeling of Epipodophyllotoxin Derivatives Using Variable Section k Nearest Neighbor QSAR Method," Journal of Medicinal Chemistry (2002), 45(11), 2294-2309, CODEN: JMCMAR; ISSN: 0022-2623, American Chemical Society, Natural Products Laboratory Division of Medicinal Chemistry and Natural Products School of Pharmacy, Chapel Hill, North Carolina.
Li et al., "Reactions of podophyllotoxin with DDQ," Chinese Chemical Letters (2001), 12(12), 1057-1060, CODEN: CCLEE7; ISSN: 1101-8417, Chinese Chemical Society, Structure Research Laboratory, University of Science and Technology of China, Hefei, China.
Pan et al., "Synthesis of epipodophyllotoxin carboxylates and antitumor activity in vitro," Yaoxue Xuebao (1997), 32(12), 898-901, CODEN: YHHPAL; ISSN: 0513-4870, Chinese Academy of Medical Sciences, Institute of Materia Media, Department of Chemistry, Zhejian University, Hangzhou, China.
Pan et al., "Synthesis and antitumor activity of new derivatives of podophyllotoxin," Current Science (1997), 72(4), 268-271, CODEN: CUSCAM; ISSN: 0011-3891, Current Science Association, Department of Chemistry, Zhejiang University, Hangzhou, China.
Cho et al., Antitumor Agents. 163. Three-dimensional quantitative structure-activity relationship study of 4'-O-demethylepipodophyllotoxin analogs using the modified CoMFA/q2-GRS approach, Journal of Medicinal Chemistry (1996), 39(7), 1383-95, CODEN: JMCMAR; ISSN: 0022-2623, American Chemical Society, School of Pharmacy, University of North Carolina, US.
Gan et al., "Inhibition of tumor necrosis factor-alpha (TNF-α) and interleukin-1 beta (IL-β) secretion but not IL-6 from activated human peripheral blood monocytes by a new synthetic demethylpodophyllotoxin derivative," Journal of Clilnical Immunology (1994), 14(5), 280-8, CODEN: JCIMDO; ISSN: 0271-9142, UCLA School Medicine, University California, US.
Yin et al., "Synthesis and antitumor activity of 4-O-(halogenated) acyl-4'-demethylepipodophyllotoxin analogs," Yaoxue Xuebao (1993), 28(10), 758-61, CODEN: YHHPAL; ISSN: 0513-4870, Shanghai Inst. Pharm. Ind., Shanghai, China.

(Continued)

*Primary Examiner*—D. Margaret Seaman
*Assistant Examiner*—Nizal S Chandrakumar
(74) *Attorney, Agent, or Firm*—Swiss Tanner, P.C.

(57) ABSTRACT

4-O esters of podophyllotoxin and 4'-demethylepipodophyllotoxin are provided. The compounds are 4-O esters of an alkanoic acid or substituted alkanoic acid and podophyllotoxin and 4'-demethylepipodophyllotoxin. The compounds are useful for treating cancer.

20 Claims, No Drawings

OTHER PUBLICATIONS

Gan et al., "Selective inhibition of TNF-alpha and IL-1-beta synthesis and secretion from activated human monocytes by a new synthetic demethylpodophyllotoxin derivative," European Cytokine Network, (1994), vol. 5, No. 2, pp. 207; Meeting Info.: 5$^{th}$ International Congress on Tumor Mecrosis Factor, California, US, ISSN: 1148-5493.

Brodin, et al. "In vitro release studies on lidocaine aqueous solutions, micellar solutions, and o/w emulsions". *Acta Pharm Suec.* 19: 267-284 (1982).

Fischer, et al. "Preparation of peptide derivatives for improved delivery of drug therapeutic agents". Abstract, CA 132:93654 (2000).

Forssen, et al. "Selective in Vivo Localization of Daunorubicin Small Unilamellar Vesicle in Solid Tumors". *Cancer Res,* 52: 3255-3261 (1992).

Fung, et al. "Perfluorochemical Emulsions with Fluorinated Surfactants and Anticancer Drugs". *Biomater. Artif. Cells. Artif. Organs* 16(1-3): 439-440 (1988).

Gensler, et al. "Nonenolizable Podophyllotoxin Derivates". *J. Med. Chem.* 20(5): 635-644 (1977).

Greenwald, et al. "Drug delivery of anticancer agents: water soluble 4-polyethylene glycol derivatives of the lignan, podophyllotoxin." Abstract, CA 132:15517 (1999).

Hansen, et at. "New Compounds Related to Podophyllotoxin and Congeners: Synthesis, Structure Elucidation and Biological Testing". *Acta Chemi. Scand.* 47: 1190-1200 (1993).

Khokhar, et al. "Chemical and Biological Studies on a Series of Lipid-Soluble (trans-(R,R)- and -(S,S)-1,2-Diaminocyclohexane)platinum(II) Complexes Incorporated in Liposomes". *J. Med. Chem,* 34: 325-329 (1991).

Lasic. "Mixed micelles in drug delivery". *Nature* 335: 279-280 (1992).

Lee, et al. "Anti-aids Agents. 29. Anti-HIV Activity of Modified Podophyllotoxin Derivatives". *Bio & Med. Chem.* Ltrs. 7(22): 2897-2902 (1997).

Levy, et al. "Antitumor agents. LXII: Synthesis and biological evaluation of podophyllotoxin esters and related derivatives". *J. Pharm. Sci.* 72(10): 1158-1161(1983).

Lie, et al. "Synthesis and spectral characteristics of some unusual fatty esters of podophyllotoxin". CA 132:3273.

Mantle. "Therapeutic applications of medicinal plants in the treatment of breast cancer: a review of their pharmacology, efficacy and tolerability". PMID: 11059361 (2000).

Nagao, et al. "Different mechanisms of action of long chain fatty acid esters of podophyllotoxin and esters of epipodophyllotoxin against P388 lymphocytic leukemia in mice." Medicinal Chemistry Research, 1(4): 295-9 (1991).

Nagao, et al. "Preparation and testing of podophyllotoxin derivatives as neoplasm inhibitors." CA 112:7272 (1990).

Pan, et al. "Synthesis of epipodophyllotoxin carboxylates and antitumor activity in vitro". Abstract, CA 129: 175488 (1998).

Pan, et al. STN Accession No. 1998:291310; Document No. 129:175488; Abstract of Yaoxue Xuebao, 1997, 32(12), 898-901.

Perez-Soler, et al. "Anthracycline Antibodies with High Liposome Entrapment: Structural Features and Biological Activity". *Cancer Res.,* 50:4260-4266 (1990).

Pradhan. "SN Effect of Various Drugs on the Tumor-necrotizing Activity of Several Chemical Agents in Mice". Cancer Research (1956) 1062-8.

Santangelo, et al. "A convenient synthesis of phosphate esters of dopamine and epinine". *Syn. Comm.,* 26(15): 2863-2873 (1996).

Supersaxo, et al. "Mixed Micelles as a Proliposomal, Lymphotropic Drug Carrier". *Pharm Res.* 8(10): 1280-1291 (1991).

Thurston, et al. "Antitumor Agents. 100. Inhibition of Human DNA Topoisomerase II by Cytotoxin Ether and Ester Derivatives of Podophyllotoxin and α-Peltatin". *J. Med. Chem.* 32: 604-608 (1989).

Wang, et al. "Syntheses and structure-activity relationship of podophyllotoxin derivatives as potential anticancer drugs". Abstract, CA 127:149030 (1997).

Weller, et al. "21-day oral Etoposide for metastatic breast cancer: a phase II study and review of the literature". PMID: 10857889 Am J Clin Oncol. 23(3): 258-62 (2000).

Yokoyama, et al. "Toxicity and Antitumor Activity against Solid Tumors of Micelle-forming Polymeric Anticancer Drug and Its Extremely Long Circulation in Blood". *Cancer Res.* 51:3229-3236 (1991).

Gupta, et al. "Synthesis and biological activities of the C-4 esters of 4'-demethylepipodophyllotoxin". Anti-Cancer Drug Design, 2(1): 13-23 (1987).

Leighton, et al. "Effects of a podophyllotoxin derivative on tissue culture systems in which human cancer invades normal tissue". Abstract, Cancer Research 17: 336-44(1957).

Wang, et al. "New spin labeled analogs of podophyllotoxin as potential antitumor agents". Life Sciences, GB, 61(5): 537-542 (1997).

Yoo, et al. "Immunoassay of podophyllotoxin". Journal of Natural Products, 56(5): 715-21 (1993).

* cited by examiner

PODOPHYLLOTOXIN DERIVATIVES

CROSS-REFERENCE TO RELATED APPLICATION

This application is a Divisional Application of the copending U.S. Utility patent application Ser. No. 10/612,240, filed Jul. 1, 2003, which is hereby incorporated by reference in its entity.

STATEMENT AS TO RIGHTS TO INVENTIONS MADE UNDER FEDERALLY-SPONSORED RESEARCH AND DEVELOPMENT

The U.S. Government has a paid-up license in this invention and the right in limited circumstances to require the patent owner to license others on reasonable terms as provided for by the terms of grant number DAMD-99-1-9018, awarded by the U.S. Army Medical Research Acquisition Activity.

INTRODUCTION

1. Field of the Invention

This invention relates to novel derivatives of podophyllotoxin that are useful for treating various types of cancer.

2. Background of the Invention

Podophyllotoxin is a known compound having the formula:

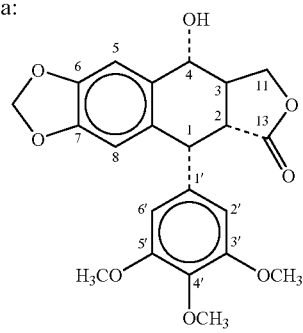

The compound shows activity as an antiviral and as an antineoplastic agent. This invention relates to novel derivatives of the compound that are useful for treating cancer.

SUMMARY OF THE INVENTION

One aspect of the invention is a compound represented by the formula:

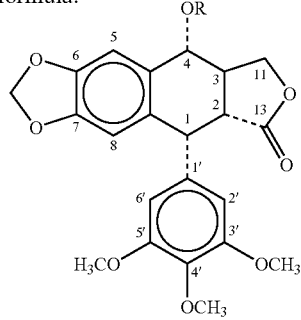

where R is $C(O)-(CH_2)_m-X-R_1$, wherein m is 0-10, X is S, O, N or a covalent bond, and $R_1$ is optionally substituted phenyl, optionally substituted cycloalkyl having 3 to 7 carbons forming the ring, optionally substituted fused 2-, 3-, or 4-ring heterocycle, optionally substituted 1- or 2-naphthyl, optionally substituted 5- or 6-membered heterocycle, optionally substituted anthraquinone, or hemisuccinic acid, with the proviso that when m is 0 and X is a bond, $R_1$ cannot be phenyl or substituted phenyl; when X is a bond and $R_1$ is phenyl, m cannot be 2 and when X is O, m cannot be 1.

Another aspect of the invention is a compound represented by the formula:

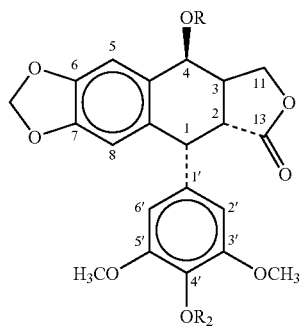

where R is $C(O)-(CH_2)_m-X-R_1$, wherein m is 0-10, X is S, O, N or a covalent bond, and $R_1$ is optionally substituted phenyl, optionally substituted cycloalkyl having 3 to 7 carbons forming the ring, optionally substituted fused 2-, 3-, or 4-ring heterocycle, optionally substituted 1- or 2-naphthyl, optionally substituted 5- or 6-membered heterocycle, optionally substituted anthraquinone, hemisuccinic acid; and $R_2$ is hydrogen, $PO_3H_2$ or $PO(OR_3)_2$ where $R_3$ is benzyl.

Another aspect of this invention is a compound of the formula A-$R_5$—B wherein each of A and B independently is represented by the radical

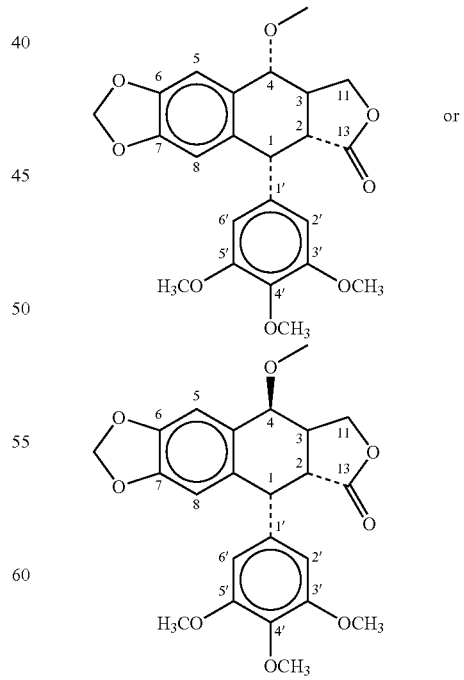

wherein $R_2$ is hydrogen, $PO_3H_2$ or $PO(OR_3)_2$ where $R_3$ is benzyl and $R_5$ is a dicarboxy linker.

Another aspect of the invention is a pharmaceutical composition useful for treating cancer in a warm-blooded animal, which composition comprises compound of the invention as defined herein in combination with a pharmaceutically acceptable excipient.

Another aspect of this invention is a method for treating cancer in a warm-blooded animal, which method comprises administering a therapeutically effective amount of a compound of the invention as defined herein. The compound is administered in a therapeutically effective dose by appropriate administration, e.g. orally, topically, or parenterally.

Another aspect of this invention is a process for preparing compounds of this invention by reacting podophyllotoxin (PT) or 4'-demethylepipodophyllotoxin (DPT) with a compound of the formula $YC(O)(CH_2)_m XR_1$, wherein m, X, and $R_1$, are as defined herein, and Y is e.g. bromide, chloride, hydroxy, or alkoxy. Preferably Y is OH.

Other aspects of this invention will be apparent to one of skill in the art by reviewing the ensuing specification.

DETAILED DESCRIPTION

Overview

In general this invention can be viewed as derivatives of podophyllotoxin or 4'-demethylepipodophyllotoxin. The novel compounds of the invention are active against tumors in mice and are generally well tolerated. They are useful for treating various types of cancer and can be formulated to prepare pharmaceutical preparations, e.g. for oral, topical, or parenteral administration.

While not wishing to be bound by any particular mechanism of action or theoretical explanation of how the compounds work, it is believed that the principal mechanism of action of the compounds of the invention is the inhibition of the catalytic activity of type II DNA topoisomerase (topoisomerase II) and concurrent enzyme-mediated production of lethal DNA strand breaks.

Definitions

The term "alkyl" refers to a monovalent, saturated aliphatic hydrocarbon radical having the indicated number of carbon atoms. For example, a "C 1-6 alkyl" or an "alkyl of 1-6 carbons" or "Alk 1-6" would refer to any alkyl group containing one to six carbons in the structure. "C 1-20 alkyl" refers to any alkyl group having one to twenty carbons. Alkyl may be a straight chain (i.e. linear) or a branched chain. Lower alkyl refers to an alkyl of 1-6 carbons. Representative examples lower alkyl radicals include methyl, ethyl, n-propyl, n-butyl, n-pentyl, n-hexyl, isopropyl, isobutyl, isopentyl, amyl, sec-butyl, tert-butyl, tert-pentyl and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted with substituents at positions that do not significantly interfere with the preparation of compounds falling within the scope of this invention and that do not significantly reduce the efficacy of the compounds. The alkyl may be optionally substituted with one to five substituents independently selected from the group consisting of halo, lower alkoxy, hydroxy, cyano, nitro, or amino.

The term "alkoxy" refers to a monovalent radical of the formula RO—, where R is an alkyl as defined herein. Lower alkoxy refers to an alkoxy of 1-6 carbon atoms, with higher alkoxy is an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted with substituents at positions that do not significantly interfere with the preparation of compounds falling within the scope of this invention and that do not significantly reduce the efficacy of the compounds. The radical may be optionally substituted with one to five substituents independently selected from the group consisting of halo, lower alkyl, lower alkoxy, hydroxy, cyano, nitro, or amino.

The term "cycloalkyl" refers to a monovalent, alicyclic, saturated hydrocarbon radical having three or more carbons forming the ring. While known cycloalkyl compounds may have up to 30 or more carbon atoms, generally there will be three to seven carbons in the ring. The latter include, for example, cyclopropyl, cyclobutyl, cyclopentyl, cyclohexyl, and cycloheptyl. The radical may be optionally substituted with substituents at positions that do not significantly interfere with the preparation of compounds falling within the scope of this invention and that do not significantly reduce the efficacy of the compounds. The cycloalkyl is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

The term "hydroxycarbonyl" is a monovalent radical having the formula —C(O)OH.

The term "lower alkoxycarbonyl" is a monovalent radical having the formula —C(O)OAlk, where Alk is lower alkyl.

The term "lower alkylcarboxyloxy" is a monovalent radical having the formula —OC(O)Alk, where Alk is lower alkyl.

The term "lower alkylcarbonylamino" is a monovalent radical having the formula —NHC(O)Alk, where Alk is lower alkyl.

The term "alkylamino" is a monovalent radical having the formula —$NR_1$, $R_2$ where $R_1$ is alkyl and $R_2$ is hydrogen or alkyl and the alkyl is optionally substituted.

A "halo" substituent is a monovalent halogen radical chosen from chloro, bromo, iodo, and fluoro. A "halogenated" compound is one substituted with one or more halo substituent.

A "phenyl" is a radical formed by removal of a hydrogen from a benzene ring. The phenyl is optionally substituted with from one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino. The phenyl may also be substituted by a camptothecin or a camptothecin derivative through a carbonyl group attached to the E ring of the camptothecin at the 20 S-oxygen. Such compound are known in the art, see, for example, U.S. Pat. No. 6,350,756 or 6,403,604, which incorporated herein by reference in their entirety.

A "dicarboxy linker" is a divalent radical having two carboxy groups (C(O)—) that link two molecules such as podophyllotoxin or 4'-demethylepipodophyllotoxin together at an oxygen linkage, e.g., the 4-position of the podophyllotoxin molecule. Such linkers include straight chain or cyclic linkers and include by way of example 5-nitroisophthalic acid and 3,5 pyridine dicarboxylic acid.

A "carbamoyloxy" is a monovalent radical of the formula $R_{13}R_{14}NC(O)O$— (i.e. an aminocarbonyloxy) where $R_{13}$ and $R_{14}$ together form a cyclic amino with the nitrogen atom, or each of $R_{13}$ and $R_{14}$ is independently hydrogen, lower alkyl, hydroxy lower alkyl, hydroxy lower alkyl, amino lower alkyl, lower cycloalkyl, phenyl (substituted or unsubstituted), or benzyl (substituted or unsubstituted). Examples include aminocarbonyloxy, methylaminocarbonyloxy, dimethyl aminocarbonyloxy, [4-(1-piperidino)-1-piperidino]carbonyloxy, 1-morpholinocarbonyloxy, 1-pyrrolidinyl, 1-piperazinecarbonyloxy, and others delineated herein.

A "5-membered heterocyclic ring" is a monovalent radical of a 5-member closed ring containing carbon and at least one other element, generally nitrogen, oxygen, or sulfur and may be fully saturated, partially saturated, or unsaturated (i.e. aromatic in nature). Generally the heterocycle will contain no more than two hetero atoms. Representative examples of unsaturated 5-membered heterocycles with only one hetero atom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolidinyl, 2- or 3-tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. The heterocyclic radical is bonded through an available carbon atom in the heterocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino. Excluded from the definition is a compound that is a carbocyclic imide compound such as succinimide or a hemi-succinimide.

A "6-membered heterocyclic ring" is a monovalent radical of a 6-member closed ring containing carbon and at least one other element, generally nitrogen, oxygen, or sulfur and may be fully saturated, partially saturated, or unsaturated (i.e. aromatic in nature). Generally the heterocycle will contain no more than two hetero atoms. Representative examples of unsaturated 6-membered heterocycles with only one hetero atom include 2-, 3-, or 4-pyridinyl, 2H-pyranyl, and 4H-pyranyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4-pyridazinyl, 2-, 4-, or 5-pyrimidinyl, 2-pyrazinyl, and the like. The corresponding fully saturated and partially saturated radicals are also included, e.g. 2-piperazine. The heterocyclic radical is bonded through an available carbon atom in the heterocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino. Excluded from the definition is a compound that is a cyclic imide compound such as succinimide or a hemi-succinimide.

The term "2-, 3- or 4-ring fused heterocycle" is a 5-, 6-, or 7-membered heterocyclic ring fused to another, carbocyclic ring or rings or another such 5-, 6-, or 7-membered heterocyclic ring. Representative examples include chromone, quinoline, 1,2,3,4-tetrahydro-carboline, 1,2,3,4-tetrahydroisoquinoline, benzofuran, and the like.

A "cyclic amino" is a monovalent radical of a saturated 5-, 6-, or 7-membered cyclic amine ring having no more than one additional hetero atom such as nitrogen, oxygen, or sulfur. Representative examples include, e.g., 1-pyrrolidino, 1-piperidino, morpholino, piperazino, 3-benzylpiperidino, and the like. These may be substituted or unsubstituted. If substituted, generally they will have no more than 2 substituents chosen from lower alkyl, lower cycloalkyl, hydroxy lower alkyl, phenyl (substituted or unsubstituted), benzyl (substituted or unsubstituted), aminocarbonylmethyl, lower alkylaminocarbonylmethyl, amino, mono- or di-lower alkylamino, cyclic amino, or a 5- or 6-membered heterocyclic ring.

An "imide ring" is a cyclic imide wherein the nitrogen of the cyclic structure is bonded on each side to a carbonyl group, which in turn is bound to carbon atoms to form a ring. An aromatic fused imide ring would include, e.g. phthalimide (which may be substituted on the benzene ring), 1,8-naphthalimide (which may be substituted on the naphthyl ring—e.g. 3-nitro-1,8-naphthalimide, 4-nitronaphthalimide, 4-bromo-naphthalimide, and the like). Others will be apparent to one of skill in the art. A carbocyclic imide would include maleimide, succinimide, hemisuccinimide, and the like.

Other chemical terms are given their standard meaning as understood by one of skill in the art with guidance from standard texts and dictionaries.

The term "MTD" is the abbreviation for maximum tolerated does.

The term "nM" is the abbreviation for nanomolar.

The term "ip" is the abbreviation for intraperitoneal.

Compounds of the Invention

One aspect of the invention is a compound represented by the formula (I):

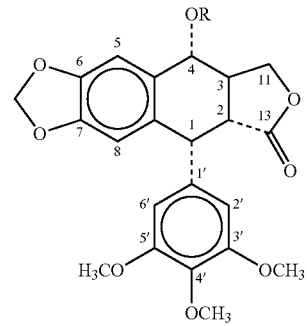

where R is $C(O)—(CH_2)_m—X—R_1$, wherein m is 0-10, X is S, O, N or a covalent bond, and $R_1$ is optionally substituted phenyl, optionally substituted cycloalkyl having 3 to 7 carbons forming the ring, optionally substituted fused 2-, 3-, or 4-ring heterocycle, optionally substituted 1- or 2-naphthyl, optionally substituted 5- or 6-membered heterocycle, optionally substituted anthraquinone, or hemisuccinic acid; with the proviso that when m is 0 and X is a bond, $R_1$ cannot be phenyl or substituted phenyl; when X is a bond and $R_1$ is phenyl, m cannot be 2 and when X is O, m cannot be 1.

Another aspect of the invention is a compound represented by the formula (II):

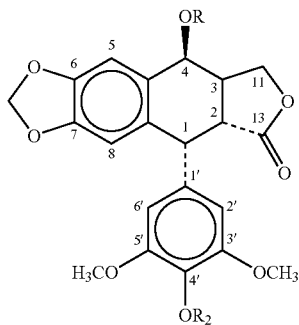

where R is C(O)—(CH$_2$)$_m$—X—R$_1$, wherein m is 0-10, X is S, O, N or a covalent bond, and R$_1$ is optionally substituted phenyl, optionally substituted cycloalkyl having 3 to 7 carbons forming the ring, optionally substituted fused 2-, 3-, or 4-ring heterocycle, optionally substituted 1- or 2-naphthyl, optionally substituted 5- or 6-membered heterocycle, optionally substituted anthraquinone, hemisuccinic acid; and R$_2$ is hydrogen, PO$_3$H$_2$ or PO(OR$_3$)$_2$ where R$_3$ is benzyl.

Another aspect of this invention is a compound of the formula A-R$_5$—B wherein each of A and B independently is represented by the radical

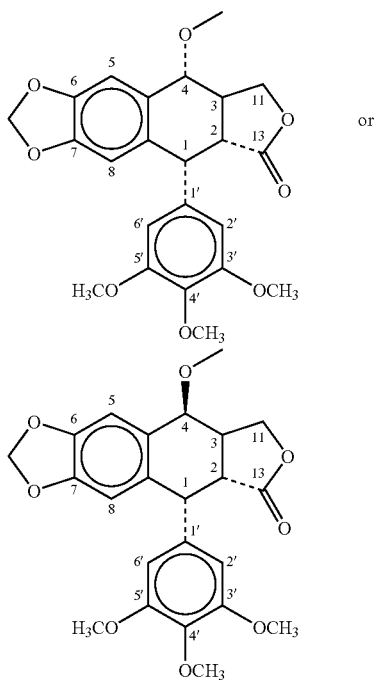

wherein R$_2$ is hydrogen, PO$_3$H$_2$ or PO(OR$_3$)$_2$ where R$_3$ is benzyl and R$_5$ is a dicarboxy linker.

A preferred aspect is a compound of formula (I) or formula (II) wherein m is 1-10 and R$_1$ is phenyl substituted with one to five substituents independently selected from halo, lower alkyl, hydroxy, lower alkoxy, cyano, nitro, amino, lower alkylamino, halogenated lower alkylamino, halogenated lower alkyl, halogenated lower alkoxy, carbonyl, hydroxycarbonyl, lower alkylcarbonyloxy, benzyloxy, optionally substituted 5- or 6-membered heterocyclic ring, an imide ring, lower alkoxycarbonyl, and lower alkylcarbonylamino.

The compounds wherein m is an integer of 1-3 (preferably 1) and X is S or preferably O are of particular interest, when R$_1$ is phenyl, it is preferably substituted with 0-3 substituents independently chosen from halo, methyl, methoxy, NO$_2$, trifluoromethyl, and carboxyl. Specific examples are formed in the Examples.

Another preferred aspect is a compound of formula (I) or formula (II) wherein m is 1 and R$_1$ is optionally substituted cycloalkyl having 3 to 7 carbons forming the ring, optionally substituted fused 2-, 3-, or 4-ring heterocycle, optionally substituted 5- or 6-membered heterocycle, or optionally substituted anthraquinone.

Another aspect of this invention is a compound of Formula (I) or (II) where R is C(O)—(CH$_2$)M-X—R' where m is 0, X is a covalent bond and R' is a phenyl substituted by a camptothecin or a camptothecin derivative through a carbonyl group attached to the E ring of the camptothecin at the 20 S-oxygen.

This is visualized by referencing U.S. Pat. No. 6,350,756 at columns 7 and 8, which results in a compound of formula (I) or formula (II), where R is C(O)—(CH$_2$)$_m$—X—R$_1$, wherein m is 0, X is a covalent bond, and R$_1$ is

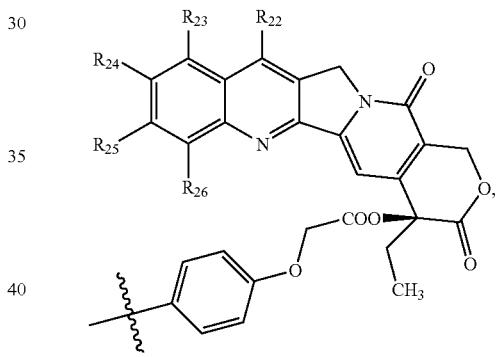

R$_{22}$ is hydrogen, halo, lower alkyl, lower alkoxy, hydroxy, R$_{40}$C(O)O, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, mono- or di-alkylcarbonyl, alkylcarbonylmethyl, benzoylmethyl, benzylcarbonyloxymethyl, or mono- or di lower alkoxymethyl;

R$_{23}$ is hydrogen, halo, lower alkyl, lower alkoxy, hydroxy, R$_{40}$C(O)O, cyano, nitro, amino, halogenated lower alkyl, halogenated lower alkoxy, hyroxycarbonyl, formyl, lower alkoxycarbonyl, CH$_2$NR$_{27}$R$_{28}$ (where each of R$_{27}$ and R$_{28}$ is independently H—, alkyl of 1-6 carbons, optionally substituted phenyl, hydroxy lower alkyl, amino lower alkyl, or mono- or dialkylamino lower alkyl, or R$_{27}$ and R$_{28}$ taken together with —N— represent a cyclic amino-), CH$_2$R$_{29}$ (where R$_{29}$ is lower alkoxy, CN, amino lower alkoxy, mono- or di-lower alkylamino lower alkoxy, lower alkylthio, amino lower alkylthio, or mono- or di-lower alkylamino lower alkylthio), or NR$_{30}$R$_{31}$ (where each of R$_{30}$ and R$_{31}$ is independently hydrogen, lower alkyl, phenyl, hydroxy lower alkyl, amino lower alkyl, or mono- or di-lower alkyl, or R$_{30}$ and R$_{31}$ taken together with —N— represent a cyclic amino), dialkylamino alkyl, lower alkylcarbonyloxy, or lower alkylcarbonylamino;

$R_{24}$ is hydrogen, halo, lower alkyl, lower alkoxy, hydroxy, $R_{40}C(O)O$, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R_{24}$ together with $R_{25}$ is methylenedioxy;

$R_{25}$ is hydrogen, halo, lower alkyl, lower alkoxy, hydroxy, $R_{40}C(O)O$, cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and $R_{26}$ is hydrogen, halo, lower alkyl, lower alkoxy, hydroxy, $R_{40}C(O)O$, cyano, nitro, amino, halogenated lower alkyl, halogenated lower alkoxy, hydroxycarbonyl, formyl, lower alkoxycarbonyl, lower alkylcarbonyloxy, or lower alkylcarbonylamino;

$R_{40}$ is $R_{41}$—O—$(CH_2)_s$—;

s is an integer of 1-10;

$R_{41}$ is lower alkyl;

phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino;

cycloalkyl of 3-7 carbons, optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; and a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

wherein the wavy line represents the point of connection to X.

Some aspects of the invention include compounds as described hereinbefore. These include, for example, the preferred subgroups set forth hereinafter:

The compound of formula (I) or (II), wherein $R_{26}$ is hydrogen, particularly a compound wherein $R_{24}$ and $R_{25}$ together are methylenedioxy and wherein $R_{22}$ is hydrogen. Of these the compounds of particular interest are those where $R_{23}$ is nitro, amino, methyl, chloro, cyano, acetoxy, or acetylamino.

A compound of formula (I) or (II), wherein each of $R_{25}$ and $R_{26}$ is hydrogen, especially those wherein $R_{23}$ is hydrogen; $R_{22}$ is (3-chloro-n-propyl)dimethylsilyl, tert-butyldimethylsilyl, acetoxymethyl, cyano, formylethenyl, ethoxycarbonylethenyl, cyanoethenyl, 2,2-dicyanoethenyl, (2-cyano-2-ethoxycarbony)ethenyl, ethoxycarbonylethyl, methyl, ethyl, or n-propyl; and $R_{24}$ is hydroxy, acetoxy, amino, nitro, cyano, chloro, bromo, fluoro, lower alkyl, higher alkyl, lower alkoxy, carbamoyloxy, or formyl. Of these, the compounds wherein $R_{22}$ is ethyl and $R_{24}$ is carbamoyloxy are of further interest. Carbamoyloxy substituents that are preferred include 1-piperazinocarbonyloxy, 4-(i-propylaminocarbonylmethyl)piperazin-1-yl-carbonyloxy, or 4-(1-piperidino)-1-piperidinocarbonyloxy.

The compound of formula (I) or (II), wherein each of $R_{22}$, $R_{25}$, and $R_{26}$ is hydrogen, for example, those wherein $R_{23}$ is amino, nitro, cyano, halo, OH, lower alkylamino, di-lower alkylamino, lower alkyl, lower alkoxy, 1-piperidino, 1-morpholino, aminomethyl, lower alkylaminomethyl, cycloalkylaminomethyl, di-lower alkylaminomethyl, cyclic aminomethyl, acetoxy, acetylamino, lower alkoxymethyl, omega hydroxy lower alkylaminomethyl, cyanomethyl and $R_{24}$ is hydroxy, acetoxy, cyano, nitro, amino, halo, formyl, lower alkoxy, carbamoyloxy.

A compound wherein each of $R_{22}$, $R_{23}$, $R_{25}$ and $R_{26}$ is hydrogen and $R_{24}$ is —OC(O)alkyl$_{1-20}$.

Thus, in one embodiment, $R_{22}$ is hydrogen;

$R_{23}$ is $CH_2NR_{27}R_{28}$ (where each of $R_{27}$ and $R_{28}$ is independently H—, alkyl of 1-6 carbons, optionally substituted phenyl, hydroxy lower alkyl, amino lower alkyl, or mono- or dialkylamino lower alkyl, or $R_{27}$ and $R_{28}$ taken together with —N— represent a cyclic amino-), $NR_{30}R_{31}$ (where each of $R_{30}$ and $R_{31}$ is independently hydrogen, lower alkyl, phenyl, hydroxy lower alkyl, amino lower alkyl, or mono- or di-lower alkyl, or $R_{30}$ and $R_{31}$ taken together with —N— represent a cyclic amino), or dialkylamino alkyl;

$R_{24}$ is lower alkoxy, hydroxy, halogenated lower alkyl, halogenated lower alkoxy, hydroxycarbonyl, formyl, lower alkoxycarbonyl, carbamoyloxy, lower alkylcarbonyloxy, or $R_{24}$ together with $R_{25}$ is methylenedioxy;

$R_{25}$ is hydrogen, or together with $R_{24}$ is methylenedioxy; and $R_{26}$ is hydrogen.

In another embodiment, where each of $R_{25}$ and $R_{26}$ is hydrogen, $R_{23}$ is $CH_2NR_{27}R_{28}$ (where each of $R_{27}$ and $R_{28}$ is lower alkyl), and $R_{24}$ is hydroxy, alkoxy or alkylcarbonyloxy. A representative compound is where $R_{23}$ is $CH_2N(CH_3)_2$ and $R_{24}$ is hydroxy.

In another embodiment, $R_{22}$ is hydrogen, lower alkyl, or halogenated lower alkyl;

$R_{23}$ is hydrogen or lower alkyl;

$R_{24}$ is lower alkoxy, hydroxy, halogenated lower alkoxy, carbamoyloxy, lower alkylcarbonyloxy, or $R_{24}$ together with $R_{25}$ is methylenedioxy;

$R_{25}$ is hydrogen, or together with $R_{24}$ is methylenedioxy; and $R_{26}$ is hydrogen.

A representative compound is where each of $R_{23}$, $R_{25}$ and $R_{26}$ is hydrogen, $R_{22}$ is alkyl, such as ethyl, and $R_{24}$ is carbamoyloxy, such as 4-(1-piperazino)-1-piperidino-carbonyloxy.

In yet another embodiment, $R_{22}$ is lower alkyl, e.g., ethyl;

each of $R_{23}$, $R_{25}$, and $R_{26}$ is hydrogen; and $R_{24}$ is hydroxy, lower alkoxy, halogenated lower alkoxy, hydroxycarbonyl, formyl, lower alkoxycarbonyl, carbamoyloxy, or lower alkylcarbonyloxy, particularly hydroxy.

In yet another embodiment,
each of $R_{22}$, $R_{24}$, $R_{25}$, and $R_{26}$ is hydrogen; and
$R_{23}$ is amino or nitro.

In yet another embodiment,
$R_{22}$ is tri-lower alkylsilyl, such as t-butyldimethylsilyl;
each of $R_{23}$, $R_{25}$ and $R_{26}$ is hydrogen; and
$R_{24}$ is hydroxy, lower alkoxy, halogenated lower alkoxy, hydroxycarbonyl, formyl, lower alkoxycarbonyl, carbamoyloxy, or lower alkylcarbonyloxy, particularly hydroxy.

The compounds of formula (I) or formula (II) wherein m is an integer of 0-3 (preferably 1) and X is oxygen or a covalent bond are of particular interest. These compounds are of particular interest when X is a covalent bond and $R_1$ is an optionally substituted 5- or 6-membered heterocycle with an oxygen or one or two nitrogens in the ring, a fused heterocyclic ring system, or a fused carbocyclic system. Specific examples are formed in the Examples.

Pharmaceutical Composition of the Invention

This aspect of the invention is a pharmaceutical composition useful for treating cancer in a warm-blooded animal, which composition comprises compound of the invention as defined herein in combination with a pharmaceutically acceptable excipient. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention are found by reference to the 18$^{th}$ or 19$^{th}$ Edition of Remington's Pharmaceutical. Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose will contain a therapeutically effective amount sufficient to treat cancer in a subject and may contain from about 1.0 to 1000 mg of compound, for example about 50 to 500 mg.

The compound will preferably be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will preferably contain about 50 to about 500 mg of a compound of Formula (I).

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5.0 to about 50% by weight (% w) in dosage units weighing between 5 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91-93 for a fuller discussion.

A compound may be administered parenterally, e.g., intravenously, intramuscularly, intravenously, subcutaneously, or intraperitoneally. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

Although the compounds of this invention tend to be water soluble, in some cases, e.g., where a compound of the invention is less water soluble, it may be useful to provide liposomal delivery. The system restrains the compound of the invention by incorporating, encapsulating, surrounding, or entrapping the compound of the invention in, on, or by lipid vesicles or liposomes, or by micelles.

Liposomes have been used successfully to administer medications to cancer patients, and have been shown to be useful clinically in the delivery of anticancer drugs such as doxorubicin, daunorubicin, and cisplatinum complexes. Forssen, et al., *Cancer Res.* 1992, 52: 3255-3261; Perex-Soler, et al., *Cancer Res.* 1990, 50: 4260-4266; and, Khokhar, et al., *J. Med. Chem.* 1991, 34: 325-329, all of which are incorporated herein in their entireties by reference.

Similarly, micelles have also been used to deliver medications to patients, (Broden et al., *Acta Pharm Suec.* 19: 267-284 (1982)) and micelles have been used as drug carriers and for targeted drug delivery, (D. D. Lasic, *Nature* 335: 279-280 (1992); and, Supersaxo et al., *Pharm Res.* 8: 1280-1291 (1991)), including cancer medications, (Fung et al., *Biomater. Artif. Cells. Artif. Organs* 16: 439 et seq. (1988); and Yokoyama et al., *Cancer Res.* 51: 3229-3236 (1991)), al of which are incorporated herein in their entireties by reference.

The liposomes and/or micelles containing the compound of the invention can be administered to a cancer patient, typically intravenously. Further guidance for preparing liposomal compositions useful in this invention may be found in U.S. Pat. No. 6,096,336, which is incorporated herein by reference.

Method of Treatment of the Invention

Another aspect of this invention is a method for treating cancer in a warm-blooded animal, which method comprises administering a therapeutically effective amount of a compound of the invention as defined herein. A compound useful in this invention is administered to an appropriate subject in need of these compounds in a therapeutically effective dose by a medically acceptable route of administration such as orally, parentally (e.g., intramuscularly, intravenously, subcutaneously, interperitoneally), transdermally, rectally, by inhalation and the like.

The term cancer is to be considered in the broadest general definition as a malignant neoplasm, an abnormal mass of tissue, the growth of which exceeds and is uncoordinated with that of normal tissues and persists in the same excessive manner after cessation of the stimuli that evoked the change. It might be added that the abnormal mass is purposeless, preys on the host, and is virtually autonomous. A cancer can also be considered as a malignant tumor. A further discussion of neoplasia is found at "Robbins Pathologic Basis of Disease," Sixth Edition, by R. S. Cotran, V. Kumar, and T. Collins, Chapter 8 (W.B. Saunders Company). This information from Chapter 8 is incorporated herein by reference. The following Table A provides examples of the types of cancers, i.e., malignant tumors or neoplasia that may be treated by administering a compound of this invention.

TABLE A

| Tissue of Origin | Malignant |
|---|---|
| Composed of One Parenchymal Cell Type | |
| Mesenchymal tumors | |
| Connective tissue and derivatives | Fibrosarcoma |
| | Liposarcoma |
| | Chondrosarcome |
| | Osteogenic sarcoma |
| Endothelial and related tissues | |
| Blood vessels | Angiosarcoma |
| Lymph vessels | Lymphangiosarcoma |
| Synovium | Synovial sarcoma |
| Mesothelium | Mesothelioma |
| Brain coverings | Invasive meningioma |
| Blood cells and related cells | |
| Hematopoietic cells | Leukemias |
| Lymphoid tissue | Malignant lymphomas |
| Muscle | |
| Smooth | Leiomyosarcoma |
| Straited | Rhabdomyosarcoma |
| Epthelial tumors | |
| Stratified squamous | Squamous cell or epidermoid carcinoma |
| Basal cells of skin or adnexa | Basal cell carcinoma |
| Epithelial lining | |
| Glands or ducts | Adenocarcinoma |
| | Papillary carcinoma |
| | Cystadenocarcinoma |
| Respiratory passages | Bronchogenic carcinoma |
| | Bronchial adenoma (carcinoid) |
| Neuroectoderm | Malignant melanoma |
| Renal epithelium | Renal cell carcinoma |
| Liver cells | Hepatocellular carcinoma |
| Urinary tract epithelium (transitional) | Transitional cell carcinoma |
| Placental epithelium (trophoblast) | Choriocarcinoma |
| Testicular epithelium (germ cells) | Seminoma |
| | Embryonal carcinoma |
| More Than One Neoplastic Cell-Mixed Tumors, Usually Derived From One Germ Layer | |
| Salivary glands | Malignant mixed tumor of salivary gland origin |
| Breast | Malignant cystosarcoma phyllodes |
| Renal anlage | Wilms tumor |
| More Than One Neoplastic Cell Type Derived From More Than One Germ Layer-Teratogenous | |
| Totipotential cells in gonads or in embryonic rests | Immature teratoma, teratocarcinoma |

The compounds of the invention are thus useful in the treatment of leukemia and solid tumors, such as colon, colorectal, ovarian, mammary, prostate, lung, kidney and also melanoma tumors. The dosage range adopted will depend on the route of administration and on the age, weight and condition of the patient being treated. The compounds may be administered, for example, by the parenteral route, for example, intramuscularly, intravenously or by bolus infusion.

As used herein, a "therapeutically effective amount" of podophyllotoxin derivatives of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on mg/m² of body surface) is described by E. J. Freireich et al., *Cancer Chemother. Rep.*, 50(4):219 (1966). Body surface area may be approximately determined from the height and weight of an individual (see, e.g., Scientific Tables, Geigy Pharmaceuticals, Ardsley, N.Y. pp. 537-538 (1970)). A suitable dose range is from 1 to 1000 mg of equivalent per m² body surface area of a compound of the invention, for instance from 50 to 500 mg/m².

For all of the administering routes, the exact timing of administration of the dosages can be varied to achieve optimal results. Generally, if using Intralipid 20 as the carrier for the derivative, the actual dosage of derivative reaching the patient will be less. This is due to some loss of the derivative on the walls of the syringes, needles and preparation vessels, which is prevalent with the Intralipid 20 suspension. When a carrier, such as cottonseed oil is used, this above described loss is not so prevalent because the derivative does not adhere as much to the surface of syringes, etc.

Another important feature of the method provided by the present invention relates to the relatively low apparent overall toxicity of the derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

Process of the Invention

Another aspect of this invention is process for preparing compounds of this invention by reacting podophyllotoxin (PT) or 4'-demethylepipodophyllotoxin (DPT) with a compound of the formula $YC(O)(CH_2)_m XR_1$, wherein m, X, and $R_1$, are as defined herein, and Y is e.g. bromide, chloride, hydroxy, or alkoxy. Preferably Y is OH. The compound shown as $YC(O)(CH_2)_m XR_1$, can be referred to as a substituted alkanoic acid or substituted alkanoic acid derivative, e.g. where m is 1, it is substituted acetic acid or a derivative thereof, where m is 2, it is a substituted propionic acid or a derivative thereof, etc. One way that such an alkanoic acid is obtained is by reacting an appropriate $R_1XH$ compound with an omega-halosubstituted alkanoic acid ester (e.g. 3-halopropionic ester or 3-haloacetic ester), then hydrolyzing the ester to form the acid. Examples of preferred haloacetic acid or halopropionic acid esters include the ethyl ester of 2 or 3-bromo acid, 3-chloro acid, or 2 or 3-iodo acid. Other corresponding alkyl esters (e.g., methyl, propyl, and the like, are useful but ethyl is preferred). In some cases, it may be useful to prepare an acid halide from the corresponding alkanoic acid. The acid halides are obtained by reacting the corresponding acid with halogenated agents (such as $SOCl_2$, $PCl_3$, $POCl_3$, $PCl_5$, $PBr_3$, and so on). The acid chloride is preferred. Once the acid or its derivative is prepared, it is reacted with podophyllotoxin or 4'-demethylepipodophyllotoxin to form a compound of this invention. This reaction sequence can be generalized as follows:

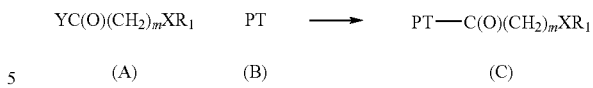

| $YC(O)(CH_2)_m XR_1$ | PT | → | $PT-C(O)(CH_2)_m XR_1$ |
|---|---|---|---|
| (A) | (B) | | (C) |

In the reaction sequence PT represents podophyllotoxin or 4'-demethylepipodophyllotoxin; Y is hydroxy, halo, or alkoxy; m is an integer of 0-10; X is oxygen, sulfur, nitrogen, or a covalent bond; and $R_1$ is as defined herein.

In the reaction sequence above, compound (A) will be used in molar excess of compound (B), e.g. a molar ratio of about 1.5:1 to about 4:1, preferably about 2:1 to 3:1. The reaction takes place in the presence of suitable coupling agent such as a carbodiimide compound, e.g. disopropylcarbodiimide, but preferably 1-(3-dimethylaminopropyl)-3-ethyl carbodiimide hydrochloride (EDCI) and 4-(dimethylamino) pyridine (DMAP) in the presence of a suitable solvent, preferably a nonaqueous, nonpolar solvent. Examples of useful solvents in this step include halogenated alkane (e.g., dichoromethane or trichloromethane) and DMF. Dichloromethane is particularly useful. The reaction temperature will range from about 20° C. to about 40° C., preferably about 20° C. to about 25° C. The time needed for the reaction to be complete will generally be no more than about 20 hours, usually less than about 10 hours.

The podophyllotoxin or 4'-demethylepipodophyllotoxin compounds are available to those of skill in the art by purchasing from Sigma-Aldrich, St. Louis, Mo. (podophyllotoxin) or Medichem China Group Company, Hong Kong (4'-demethylepipodophyllotoxin).

The compound of formula (II) may be converted to the corresponding 4'-phosphate ester as follows: A suspension of 50% NaH in mineral oil and the 4'-demethylepipodophyllotoxin-4-O-ester of formula (II) of is formed in an organic solvent. The mixture is cooled to 0° C.; a solution of dibenzylphosphorochloridate in toluene is added drop by drop. After the reaction comes to completion, the solution is diluted with cold water and extracted with ether. The ether solution is washed with water, dried, evaporated under reduced pressure to give the 4'-dibenzylphosphate derivative of the compound of formula (II). A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give a 4'-phosphate ester of a compound of formula (II).

It will be recognized by one of skill in the art that other similar compounds may be prepared by following the teachings set forth in the above articles and modifying with appropriate art-recognized steps.

Suitable alkanoic acids of formula (A) are available commercially and include the following (see the catalog by the Sigma-Aldrich Corp., St. Louis, Mo. or www.sigmaaldrich.com):

4-fluorophenoxyacctic acid;
2,4-dimethylphenoxyacetic acid;
4-methoxyphenoxyacetic acid;
4-formylphenoxyacetic acid;
2-nitrophenoxyacetic acid;
5-nitro-2-furoic acid;
3-chloroacetaminobenzoic acid;
(4-pyridylthio) acetic acid;

chromone-2-carboxylic acid;
anthraquinone-2-carbonyl chloride;
1H-tetrazole-1-acetic acid;
(4-chlorophenylthio) acetic acid;
quinoline-4-oxyacetic acid;
4-nitrophenoxyacetic acid;
3,5-ditrifluoromethylphenoxyacetic acid;
4-trifluoromethoxyphenenoxyacetic acid;
4-bromophenoxyacetic acid;
4-iodophenoxyacetic acid; phenoxyacetic acid;
2,4-dichloro-5-methylphenylthioacetic acid;
2,3,4,5,6-pentafluorophenoxyacetic acid;
3-fluoro-4-cyanophenoxyacetic acid;
3-trifluoromethyl-4-nitrophenoxyacetic acid;
4-phthalimidobenzoic acid;
3-chloro-4-bromophenoxy acetic acid;
2,6-diiodo-4-cyanophenoxyacetic acid;
4-(2-phenyl) quinolinecarboxylic acid;
phenothiazin-10-ylcarbonylchloride;
1,7-dimethyl-naphthyridin-4-one-3-carboxylic acid;
3-pyridinepropionic acid;
4-chlorophenoxyacetic acid;
3-methoxyphenoxyacetic acid;
thymine-1-acetic acid;
(+)-2-(2,4,5,7-tetranitro-9-fluorenylideneaminooxy) propionic acid;
3-phthalimidopropionic acid;
3-maleimidopropionic acid;
3-(3-nitro 1,8-naphthalimide)propionic acid;
3-(4-nitro-1,8-naphthalimide)propionic acid;
3-(4-bromo-1,8-naphthalimido)propionic acid;
3-[4-(3-trifluoromethylphenyl)-1-piperazinyl]-propionic acid;
3-[(4-benzyl)-1-piperazinyl]propionic acid;
3-[4-(3-methoxyphenyl)-1-piperazinyl]propionic acid;
3-[4-(4-nitrophenyl)-1-piperazinyl]propionic acid;
3-(4-phenyl-1-piperazinyl)propionic acid;
3-[4-(2-chlorophenyl)-1-piperazinyl]propionic acid;
3-[4-(4-fluorophenyl)-1-piperazinyl]propionic acid;
3-(1-piperidino)propionic acid;
3-[1-(4-benzyl)piperidino]propionic acid;
3-[4-(4-acetylphenyl-1-piperazinyl]propionic acid;
3-[4-(3,4-dichlorophenyl)-1-piperazinyl]propionic acid;
3-[4-(3,4-methylenedioxyphenyl)-1-piperazinyl]propionic acid;
3-[4-(4-chlorophenyl)-1-piperidinyl]propionic acid;
3-(4-formyl-1-piperazinyl)propionic acid;
3-(4-ethyl-1-piperazinyl)propionic acid;
3-[4-(4-chlorophenyl)phenylmethyl-1-piperazinyl]propionic acid;
3-(4-cyano-4-phenyl-1-piperidinyl) propionic acid;
3-trans-4-cinnamyl-1-piperazinyl) propionic acid;
3-[4-(2-methylphenyl)-1-piperazinyl]propionic acid;
3-[4-(2,3-dimethylphenyl)-1-piperazinyl]propionic acid;
3-[4-(1-piperidino)-1-piperidino]propionic acid;
3-[4-(2-pyrimidinyl)-1-piperazinyl]propionic acid;
3-(4-cyclohexyl-1-piperazinyl) propionic acid;
3-[4-(α-(2-pyridyl)benzyl-1-piperazinyl]propionic acid;
3-(4-morpholino)propionic acid;
3-(1-pyrrolinyl)propionic acid;
4-[4-(3-trifluoromethylphenyl)-1-piperazinyl]butyric acid;
5-[4-(3-trifluoromethylphenyl)-1-piperazinly]valeric acid;
and the like.

One of skill in the art will recognize that other similar 3-propionic acids and 2-acetic acids may be obtained from commercial sources or prepared by art-recognized procedures to be used in the process to prepare compounds of this invention. By reacting podophyllotoxin or 4'-demethylepipodophyllotoxin with a compound shown in the list of compounds of formula (A) in accordance with the guidelines for reaction condition, compounds of the invention will be obtained. These compounds will exhibit the desired characteristics to a greater or lesser extent. Guidance is provided herein as to the preferred subgroups of compounds within the family.

Another aspect of this invention is process for preparing compounds of this invention by following the teachings of U.S. Pat. No. 6,350,756 at columns 16, line 46, to column 18, line 19. The process is carried out by reacting podophyllotoxin (PT) or 4'-demethylepipodophyllotoxin (DPT) with a compound of the formula Y'C(O)—$(CH_2)_m R_{20}$—C(O)—CPT, wherein m is 0, $R_{20}$ is phenyoxymethyl, Y' is e.g., bromide, chloride, hydroxyl, or alkoxy, and CPT in this formula represents both camptothecin and camptothecin derivatives. Preferably, Y' is hydroxyl. When Y' is alkoxy, Y'C(O)$(CH_2)_m R_{20}$—C(O)O—CPT may be prepared by reacting camptothecin (CPT) or a CPT analog with a compound of the formula Y'C(O)$(CH_2)_m R_{20}$—C(O)$X_2$, wherein $X_2$ is e.g. bromide, chloride, or hydroxy. Preferably $X_2$ is OH. One way to prepare the compound shown as Y'C(O)—$(CH_2)_m R_{20}$—C(O)$X_2$ is by reacting an appropriate alcohol (Y'OH) with HalC(O)—$(CH_2)_m R_{20}$—C(O)$X_2$ (where $X_2$ is alkoxy), then hydrolyzing. HalC(O)—$(CH_2)_m R_{20}$—C(O)$X_2$ (where $X_2$ is alkoxy) may be prepared from the corresponding acid HO—C(O)—$(CH_2)_m R_{20}$—C(O)$X_2$ (where $X_2$ is alkoxy) via a reaction with halogenated agents (such as $SOCl_2$, $PCl_3$, $POCl_3$, $PCl_5$, $PBr_3$, and so on). The acid chloride is preferred. Once Y'C(O)$(CH_2)_m R_{20}$—C(O)$X_2$ is prepared, it is reacted with CPT or a CPT analog to form the (S)-20-ester of CPT, i.e. Y'C(O)$(CH_2)_m R_{20}$—C(O)O—CPT, which can then be used to prepare the corresponding PT or DPT esters of this invention according to the procedure described above. This reaction sequence can be generalized as follows:

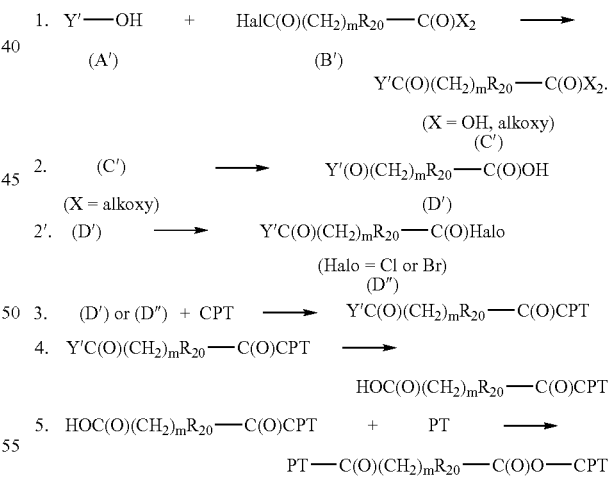

In step 1 the reaction conditions will vary depending on the exact reactants employed. In general, solvents useful in the reaction may be aqueous or nonaqueous. Preferably, a solvent will be water, an organic solvent miscible with water, or mixtures thereof. Examples of useful miscible solvents include acetone and dimethylormamide (DMF). When the solvent is aqueous, the pH of the reaction will be basic, e.g. in the range of 10 to 14, preferably about 12 to 14. The reaction temperature varies with the reactants, and the solvents, and will range from about 20° C. to about 180° C., preferably about 40° C. to about 80° C. The time needed for the reaction to be complete will generally be no more than about 10 hours, preferably about 2 to 4 hours.

In step 2, the compound of formula (C') is converted to a compound of formula (D') by a hydrolysis reaction, generally performed in two stages. The reaction conditions for this step will vary in accordance with the compound being reacted. In general, solvents useful in the conversion may be aqueous or nonaqueous, preferably, a solvent will be water, either alone or with a water-miscible organic solvent. An example of a particularly useful solvent is a mixture of water and DMF or water and dioxane. The pH of the first stage of reaction will be basic, e.g. in the range of 10 to 14, preferably about 12 to 14. A suitable inorganic base such as an alkaline earth hydroxide, e.g. sodium hydroxide, is useful. The reaction temperature will range from about 0° C. to about 60° C., preferably about 20° C. to about 25° C. The time needed for the reaction to be complete will generally be no more than 10 hours, preferably no more than about 4 hours. The mixture is then acidified to a pH of less than 4, e.g. 3, with an appropriate acid such as hydrogen chloride and extracted with a suitable solvent such as ethyl acetate in accordance with standard chemical synthetic methods. Reaction selectivity between the two esters Y'C(O)— and —C(O)$X_2$ can be achieved by using different types of groups. For example, Y'C(O)— may be $C(CH_3)_3C(O)$—, which is stable to hydrolysis under basic conditions, while —C(O)$X_2$ can be —C(O)OCH$_3$, which is liable to base hydrolysis. Such esters that can be selectively hydrolyzed are known to those skilled in the art.

In step 2', the compound of formula D' (i.e. the oxyalkanoic acid is converted into the corresponding acid halide D" by reacting with a halogenated agent such as SOCl$_2$, PCl$_3$, POCl$_3$, PCl$_5$, and PBr$_3$, and the like under appropriate conditions.

In step 3 of the process, a compound of formula (D') or (D") is reacted with CPT in about equimolar amounts under conditions suitable for the formation of the compounds of this invention as the 20-(S) stereoisomer Y'C(O)(CH$_2$)$_m$R$_{20}$—C(O)O—CPT. The reaction takes place in the presence of suitable carbodiimide compound such as diisopropylcarbodiimide, but preferably 1-(3-dimethylaminopropyl)-3-ethyl carbodiimide hydrochloride (EDCI), and 4-(dimethylamino) pyridine (DMAP) in the presence of a suitable solvent, preferably a nonaqueous, nonpolar solvent. Examples of useful solvents in this step include halogenated alkanes, e.g., dichoromethane or trichloromethane) and DMF. Dichloromethane is particularly useful. The reaction temperature will range from about 20° C. to about 40° C., preferably about 20° C. to about 25° C. The time needed for the reaction to be complete will generally be no more than about 20 hours, preferably about 10 hours.

In step 3, a suitable Camptothecin derivative or analog is a compound that is camptothecin substituted at the 7, 9, 10, 11, or 12 positions as described in this document. The camptothecin analog may be substituted with substituents known in the art or that can be prepared by one of skill in the art given the disclosure herein. Representative articles that teach how to make such analogs or where such analogs may be procured are found in the following journals (which are incorporated herein by reference): 1. J. Med. Chem. 1998, 41, 31-37 2. J. Med. Chem. 2000, 43, 3970-3980 3. J. Med. Chem. 1993, 36, 2689-2700 4. J. Med. Chem. 1991, 34, 98-107 5. J. Med. Chem. 2000, 43, 3963-3969 6. Chem. Pharm. Bull. 39(10) 2574-2580 (1991) 7. Chem. Pharm. Bull. 39(6) 1446-1454 (1991) 8. ANTIMICROBIAL AGENTS AND CHEMOTHERAPY, December 1999, p. 2862-2868 9. European Journal of Cancer, Vol. 34, No. 10, pp. 1500-1503, 1998 10. CANCER RESEARCH 55, 753-760, Feb. 15, 1995 11. Anti-Cancer Drug Design (1998), 13, 145-157 12. Bioorganic & Medicinal Chemistry Letters 8 (1998) 415-418.

Suitable camptothecin analogs include the following, where the number in parenthesis following the name refers to journal article listed above:

camptothecin (CPT);
(20S)-7-ethyl-10-[4-(1-piperidino)-1-piperidino]carbonyloxy)-CPT (AKA-irinotecan);
(20S)-9-nitro CPT (1);
(20S)-7-chloro-n-propyldimethylsilyl CPT (2);
(20S)-10-hydroxy-7-chloro-n-propyldimethylsilyl CPT (2);
(20S)-10-acetoxy-7-chloro-n-propyldimethylsilyl CPT (2);
(20S)-7-tert-butyldimethylsilyl CPT (2);
(20S)-10-hydroxy-7-tert-butyldimethylsilyl CPT (2);
(20S)-10-acetoxy-7-tert-butyldimethylsilyl CPT (2);
(20S)-9-hydroxy CPT (3);
(20S)-9-amino CPT (3);
(20S)-10-amino CPT (3);
(20S)-9-amino-10-hydroxy CPT (3);
(20S)-9-amino-10,11-methylenedioxy CPT (3);
(20S)-9-methylamino CPT;
(20S)-9-methyl CPT (3);
(20S)-9-dimethylanomethyl CPT;
(20S)-9-chloro CPT (3);
(20S)-9-fluoro CPT (3);
(20S)-9-piperidino CPT;
(20S)-9-dimethylaminomethyl-10-hydroxy CPT (3)-AKA topotecan);
(20S)-9-morpholinomethyl CPT (4);
(20S)-10-hydroxy CPT (3);
(20S)-9,10-dichloro CPT (3);
(20S)-10-bromo CPT (3);
(20S)-10-chloro CPT (3);
(20S)-10-methyl CPT (3);
(20S)-10-fluoro CPT (3);
(20S)-10-nitro CPT (3);
(20S)-10,11-methylenedioxy CPT (3);
(20S)-10-formyl CPT (3);
(20S)-10-nonylcarbonyloxy CPT (12);
(20S)-10-undecylcarbonyloxy CPT (12);
(20S)-10-pentadecylcarbonyloxy CPT (12);
(20S)-10-heptadecylcarbonyloxy CPT (12);
(20S)-10-nonadecylcarbonyloxy CPT (12);
(20S)-9-nitro-10,11-methylenedioxy CPT (3);
(20S)-9-(4-methylpiperazinylmethyl)-10-hydroxy (CPT) (4);
(20S)-9-[4-(1-piperidino)-1-piperidinomethyl]-10-hydroxy CPT (4);
(20S)-9-methyl-10,11-methylenedioxy CPT;
(20S)-9-chloro-10,11-methylenedioxy CPT (3);
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT (4);
(20S)-9-methylaminomethyl-10-hydroxy CPT;
(20S)-9-n-propylaminomethyl-10-hydroxy CPT (4);
(20S)-9-dimethylaminomethyl-10-hydroxy CPT (4);
(20S)-9-cyclohexylaminomethyl-10-hydroxy CPT (4);
(20S)-9-(2-hydroxyethyl)aminomethyl-10-hydroxy CPT (4);
(20S)-9-(trimethylammonio)methyl-10-hydroxy CPT, methanesulfonate (4);
(20S)-9-morpholinomethyl-10-hydroxy CPT (4);

(20S)-9-cyanomethyl-10-hydroxy CPT (4); (20S)-CPT-7-aldehyde (5);
(20S)-10-methoxy CPT-7-aldehyde (5);
(20S)-7-acetoxymethyl CPT (5);
(20S)-7-acetoxymethyl-10-methyl CPT (5);
(20S)-7-cyano-10-methoxy CPT (5);
(20S)-7-cyano CPT (5);
(20S)-7-formylethenyl CPT (5);
(20S)-7-ethoxycarbonylethenyl CPT (5);
(20S)-7-cyanoethenyl CPT (5);
(20S)-7-(2,2-dicyanoethenyl) CPT (5);
(20S)-7-(2-cyano-2-ethoxycarbonyl)ethenyl CPT (5);
(20S)-7-ethoxycarbonylethyl CPT (5);
(20S)-7-ethyl CPT (6);
(20S)-7-n-propyl CPT (6);
(20S)-7-acetoxymethyl CPT (6);
(20S)-7-n-propylcarbonyloxymethyl CPT (6);
(20S)-7-ethoxycarbonyl CPT (6);
(20S)-7-ethyl-10-hydroxy CPT;
(20S)-7-ethyl-10-acetyloxy CPT;
(20S)-7-methyl-10-aminocarbonyloxy CPT;
(20S)-7-n-propyl-10-piperidinocazbonyloxy CPT;
(20S)-7-ethyl-10-(2-dimethylamino)ethyl CPT; and
(20S)-7-ethyl-10-carbamoyloxy derivatives of CPT such as
(20S)-7-ethyl-10-[4(1-piperidino)-piperidino carbonyloxy CPT (7);
(20S)-7-ethyl-10-(1-piperazine)carbonyloxy CPT (7);
(20S)-7-ethyl-10-(4-1-propylaminocarbonylmethylpiperazine)carbonyloxy CPT (7);
(20S)-7-ethyl-10-[4(1-pyrrolidinyl)piperazine]carbonyloxy CPT (7);
(20S)-7-ethyl-10-[(4-dimethylamino)-1-piperidino]carbonyloxy CPT (7);
(20S)-7-ethyl-10-[4-(di-n-propylamino)-1-piperidinol]carbonyloxy CPT (7);
(20S)-7-ethyl-10-[(4-(di-n-butylamino)-1-piperidino]carbonyloxy CPT (7);
(20S)-7-ethyl-10-[4-(1-pyrrolidino)-1-piperidino)]carbonyloxy CPT (7);
(20S)-7-ethyl-10-[4-(1-piperidino)-1-piperidino]carbonyloxy CPT (7);
(20S)-7-ethyl-10-[N-methyl-N-2-(dimethylamino)ethylamino]carbonyloxy CPT (7) and the like.

In step 4, Y'C(O)(CH$_2$)$_m$R$_{20}$—C(O)O—CPT is hydrolyzed to HOC(O)(CH$_2$)$_m$R$_{20}$—C(O)O—CPT. In the case where Y' is C(CH$_3$)$_3$—O, the hydrolysis can be performed under acidic conditions using an organic solvent, such as using hydrochloric acid in methanol or trifluoroacetic acid in dichloromethane.

In step 5, HOC(O)(CH$_2$)$_m$R$_{20}$—C(O)O—CPT is reacted with PT or a PT derivative to form a compound of this invention according to the procedures described above.

Alternatively both PT or a PT derivative and a CPT or CPT derivative can react with 4-carboxylicphenoxyacetic acid in a one-pot reaction to form a mixture of products (such as PT-CO-Ph-O(CH$_2$)—C(O)—CPT, CPT-CO-Ph-O(CH$_2$)—C(O)—PT, PT-CO-Ph-O(CH$_2$)—C(O)—PT, CPT-CO-Ph-O(CH$_2$)—C(O)—CPT), which can be separated by conventional separation techniques.

EXAMPLES

The following examples are given to provide representative compounds included as part of this invention. The examples also provide descriptions of in vitro and in vivo assays to aid in determining the utility of the compounds. The compounds in examples 1-26 were prepared by reacting an appropriate acid with podophyllotoxin or the 4-demethyl epimer. Throughout the examples chemical formulas will be used to name compounds (e.g. NaHCO$_3$ is sodium bicarbonate) as appropriate.

Example 1

A. Podophyllotoxin-4-O-ester of 4-fluorophenoxyacetic acid (000615)

The mixture of podophyllotoxin (20 mg, 0.048 mmol), 4-fluorophenoxyacetic acid (17 mg, 0.1 mmol), EDCI (40 mg, 0.21 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 12 mg podophyllotoxin-4-O-4-fluorophenoxyacetate, mp.

The chemical structure analysis was performed by $^1$HNMR (CDCl$_3$, 600 MHz); δ 7.01 (t, 2H, Ar—H), 6.88 (q, 2H, Ar—H), 6.62 (s, 1H, Ar—H), 6.54 (s, 1H, Ar—H), 6.37 (s, 2H, Ar—H), 5.99 (d, 3H, OCH$_2$O), 4.73 (q, 2H, COCH$_2$O), 4.60 (d, 1H, H4), 4.34 (t, 1H, H11), 4.20 (t, 1H, H11), 3.81 (s, 3H, OCH$_3$), 3.74 (s, 6H, OCH$_3$), 2.95 (d, 1H, H2), 2.85 (m, 1H, H3).

B. 4'-demethylepipodophyllotoxin-4-O-ester of 4-fluorophenoxyacetic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 4-fluorophenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 2

A. Podophyllotoxin-4-O-ester of 4-bromophenoxyacetic acid (000320)

The mixture of podophyllotoxin (20 mg, 0.048 mmol), 4-bromophenoxyacetic acid (22 mg, 0.1 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 21 mg podophyllotoxin-4-O-4-bromophenoxyacetate, mp.

The chemical structure analysis was performed by $^1$HNMR (CDCl$_3$, 600 MHz); δ 7.42 (t, 2H, Ar—H), 6.81 (d, 2H, Ar—H), 6.62 (s, 1H, Ar—H), 6.54 (s, 1H, Ar—H), 6.37 (s, 2H, Ar—H), 5.99 (d, 3H, OCH$_2$O), 4.74 (q, 2H, COCH$_2$O, 4.60 (d, 1H, H4), 4.37 (t, 1H, H11), 4.21 (t, 1H, H11), 3.81 (s, 3H, OCH$_3$), 3.74 (s, 6H, OCH$_3$), 2.95 (d, 1H, H2), 2.85 (m, 1H, H3).

B. 4'-demethylepipodophyllotoxin-4-O-ester of 4-bromophenoxyacetic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 4-bromophenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 3

A. Podophyllotoxin-4-O-ester of 4-iodophenoxyacetic acid (000614)

The mixture of podophyllotoxin (41 mg, 0.1 mmol), 4-iodophenoxyacetic acid (55 mg, 0.2 mmol), EDCI (40 mg, 0.14 mmol), DMAP (2 mg, 0.02 mmol) and dichloromethane (5 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 35 mg podophyllotoxin-4-O-4-iodophenoxyacetate, mp.

The chemical structure analysis was performed by $^1$HNMR (CDCl$_3$, 600 MHz); δ 7.60 (t, 2H, Ar—H), 6.69 (d, 2H, Ar—H), 6.61 (s, 1H, Ar—H), 6.53 (s, 1H, Ar—H), 6.36 (s, 2H, Ar—H), 5.98 (d, 3H, OCH$_2$O), 4.74 (q, 2H, COCH$_2$O), 4.60 (d, 1H, H4), 4.34 (t, 1H, H11), 4.20 (t, 1H, H11), 3.81 (s, 3H, OCH$_3$), 3.74 (s, 6H, OCH$_3$), 2.91 (d, 1H, H2), 2.85 (m, 1H, H3).

B. 4'-demethylepipodophyllotoxin-4-O-ester of 4-iodophenoxyacetic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 4-iodophenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 4

A. Podophyllotoxin-4-O-ester of 3-chlorophenoxyacetic acid (000622)

The mixture of podophyllotoxin (20 mg, 0.048 mmol), 3-chlorophenoxyacetic acid (18 mg, 0.1 mmol), EDCI (30 mg, 0.16 mmol), DMAP (2 mg, 0.02 mmol) and dichloromethane (5 ml) were stirred in the room temperature for 20 h, then dichloromethane (20 ml) was added to the solution. Organic later was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 13 mg podophyllotoxin-4-O-3-chlorophenoxyacetate, mp.

The chemical structure analysis was performed by $^1$HNMR (CDCl$_3$, 600 MHz); δ 7.24 (t, 1H, Ar—H), 7.02 (d, 1H, Ar—H), 6.91 (s, 1H, Ar—H), 6.80 (d, 1H, Ar—H), 6.62 (s, 1H, Ar—H), 6.54 (s, 1H, Ar—H), 6.37 (s, 2H, Ar—H), 5.98 (d, 3H, OCH$_2$O, 4.74 (q, 2H, COCH$_2$O), 4.60 (d, 1H, H4), 4.34 (t, 1H, H11), 4.20 (t, 1H, H11), 3.81 (s, 3H, OCH$_3$), 3.74 (s, 6H, OCH$_3$), 2.92 (d, 1H, H2), 2.85 (m, 1H, H3).

B. 4'-demethylepipodophyllotoxin-4-O-ester of 3-chlorophenoxyacetic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 3-chlorophenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 5

A. Podophyllotoxin-4-O-ester of 4-chloro-2-methylphenoxyacetic acid (000317)

The mixture of podophyllotoxin (20 mg, 0.048 mmol), 4-chloro-2-methylphenoxyacetic acid (19 mg, 0.1 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 12 mg podophyllotoxin-4-O-4-chloro-2-methylphenoxyacetate, mp.

The chemical structure analysis was performed by $^1$HNMR (CDCl$_3$, 600 MHz); δ 7.13 (t, 2H, Ar—H), 6.66 (d, 1H, Ar—H), 6.59 (s, 1H, Ar—H), 6.54 (s, 1H, Ar—H), 6.37 (s, 2H, Ar—H), 5.99 (d, 3H, OCH$_2$O), 4.76 (q, 2H, COCH$_2$O), 4.60 (d, 1H, H4), 4.34 (t, 1H, H11), 4.20 (t, 1H, H11), 3.81 (s, 3H, OCH$_3$), 3.74 (s, 6H, OCH$_3$), 2.95 (d, 1H, H2), 2.85 (m, 1H, H3), 2.32 (s, 3H, Ar—CH$_3$).

B. 4'-demethylepipodophyllotoxin-4-O-ester of 4-chloro-2-methylphenoxyacetic acid By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 4-chloro-2-methylphenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 6

A. Podophyllotoxin-4-O-ester of 4-formylphenoxyacetic acid (000323)

The mixture of podophyllotoxin (20 mg, 0.048 mmol), 4-formylphenoxyacetic acid (11 mg, 0.061 mmol), EDCI (25 mg, 0.13 mmol), DMAP (2 mg, 0.02 mmol) and dichloromethane (3 ml) were stirred in the room temperature for 20 h, then dichlormethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 15 mg podophyllotoxin-4-O-4-formlyphenoxyacetate, mp.

The chemical structure analysis was performed by $^1$HNMR (CDCl$_3$, 600 MHz); δ 9.92 (s, 1H, CHO), 7.82 (d, 2H, Ar—H), 7.03 (d, 1H, Ar—H), 6.50 (d, 2H, Ar—H), 6.36 (s, 2H, Ar-11), 5.99 (d, 3H, OCH$_2$O), 4.86 (q, 2H, COCH$_2$O), 4.60 (d, 1H, H4), 4.40 (t, 1H, H11), 4.22 (t, 1H, H11), 3.81 (s, 3H, OCH$_3$), 3.74 (s, 6H, OCH$_3$), 2.95 (d, 1H, H2), 2.85 (m, 1H, H3).

B. 4'-demethylepipodophyllotoxin-4-O-ester of 4-formylphenoxyacetic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 4-formylphenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 7

A. Podophyllotoxin-4-O-ester of 4-methoxyphenoxyacetic acid (000329)

The mixture of podophyllotoxin (20 mg, 0.048 mmol), 4-formylphenoxyacetic acid (17.4 mg, 0.096 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting liquid was separated by column chromatography (eluent: ethyl acetate and petroleum ether) to afford 12 mg podophyllotoxin-4-O-4-formylphenoxyacetate, mp.

The chemical structure analysis was performed by $^1HNMR$ ($CDCl_3$, 600 MHz): δ 6.85 (d, 4H, Ar—H), 6.64 (s, 1H, Ar—H), 6.54 (s, 2H, Ar—H), 6.37 (s, 2H, Ar—H), 5.99 (d, 3H, $OCH_2O$), 4.70 (q, 2H, $COCH_2O$), 4.60 (d, 1H, H4), 4.34 (t, 1H, H11), 4.20 (t, 1H, H11), 3.81 (s, 3H, $OCH_3$), 3.77 (s, 3H, $OCH_3$), 3.74 (s, 6H, $OCH_3$), 2.92 (d, 1H, H2), 2.85 (m, 1H, H3).

B. 4'-demethylepipodophyllotoxin-4-O-ester of 4-methoxyphenoxyacetic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 4-methoxyphenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 8

A. Podophyllotoxin-4-O-ester of 2,4-dichlorophenoxyacetic acid (000324)

The mixture of podophyllotoxin (20 mg, 0.048 mmol), 4-formylphenoxyacetic acid (21.2 mg, 0.096 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting liquid was separated by column chromatography (eluent: ethyl acetate and petroleum ether) to afford 13 mg podophyllotoxin-4-O-2,4-dichlorophenoxyacetate, mp.

The chemical structure analysis was performed by $^1HNMR$ ($CDCl_3$, 600 MHz): δ 7.41 (d, 1H, Ar—H), 7.22 (t, 1H, Ar—H), 6.85 (d, 1H, Ar—H), 6.59 (s, 1H, Ar—H), 6.54 (s, 1H, Ar—H), 6.37 (s, 2H, Ar—H), 5.99 (d, 2H, $OCH_2O$), 4.81 (q, 2H, $COCH_2O$), 4.61 (d, 1H, H4), 4.36 (t, 1H, H11), 4.20 (t, 1H, H11), 4.15 (d, 1H, H1), 3.81 (s, 3H, $OCH_3$), 3.74 (s, 6H, $OCH_3$), 2.92 (d, 1H, H2), 2.85 (m, 1H, H3).

B. 4'-demethylepipodophyllotoxin-4-O-ester of 2,4-dichlorophenoxyacetic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 2,4-dichlorophenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 9

A. Podophyllotoxin-4-O-ester of 7-(carboxymethoxy)-3-chloro-4-methylcoumarin (000405)

The mixture of podophyllotoxin (20 mg, 0.048 mmol), 7-(carboxymethoxy)-3-chloro-4-methylcoumarin (25.8 mg, 0.096 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting liquid was separated by column chromatography (eluent: ethyl acetate and petroleum ether) to afford 16 mg podophyllotoxin-4-O-7-(3-chloro-4-methlycoumarin-7-oxyacetate), mp.

The chemical structure analysis was performed by $^1$HNMR ($CDCl_3$, 600 MHz): δ 7.59 (t, 1H, Ar—H), 6.95 (d, 1H, Ar—H), 6.84 (d, 1H, Ar—H), 6.53 (d, 2H, Ar—H), 6.36 (d, 2H, Ar—H), 5.99 (m, 2H, $OCH_2O$), 4.85 (s, 2H, $COCH_2O$), 4.61 (s, 1H, H4), 4.38 (t, 1H, H11), 4.20 (t, 1H, H11), 4.15 (d, 1H, H1), 3.81 (s, 3H, $OCH_3$), 3.74 (s, 6H, $OCH_3$) 2.92 (d, 1H, H2), 2.85 (m, 1H, H3), 2.56 (s, 3H, Ar—$CH_3$).

B. 4'-demethylepipodophyllotoxin-4-O-ester of 7-(carboxymethoxy)-3-chloro-4-methylcoumarin By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 7-(carboxymethoxy)-3-chloro-4-methylcoumarin The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 10

A. Podophyllotoxin-4-O-ester of 4-(4-dichloroethylamino) phenylbutyric acid (003132)

The mixture of podophyllotoxin (10 mg, 0.024 mmol), chlorambucil (11 mg, 0.036 mmol), EDCI (25 mg, 0.13 mmol), DMAP (2 mg, 0.02 mmol) and dichloromethane (3 ml) were stirred at 5° C. for 15 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting liquid was separated by column chromatography (eluent: ethyl acetate and petroleum ether) to afford 5 mg podophyllotoxin-4-O—[4-(4-dichloroethylamino)phenylbutyrate], mp.

The chemical structure analysis was performed by $^1$HNMR ($CDCl_3$, 600 MHz); δ 7.08 (d, 2H, Ar—H), 6.75 (s, 1H, Ar—H), 6.63 (d, 2H, Ar—H), 6.53 (s, 1H, Ar—H), 6.39 (s, 2H, Ar—H), 5.99 (d, 2H, $OCH_2O$), 5.85 (d, 1H,), 4.61 (s, H, H4), 4.35 (t, 1H, H11), 4.20 (t, 1H, H11), 3.81 (s, 3H, $OCH_3$), 3.75 (s, 6H, $OCH_3$), 2.92 (d, 1H, H2), 2.82 (m, 1H, H3), 2.56 (t, 2H, Ar—$CH_2$), 2.45 (m, 2H, $COCH_2$), 1.95 (m, 2H, $CH_2$).

B. 4'-demethylepipodophyllotoxin-4-O-ester of 4-(4-dichloroethylamino) phenylbutyric acid By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 4-(4-dichloroethylamino) phenylbutyric acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 11

A. Podophyllotoxin-4-O-ester of 3-chloroacetamidobenzoic acid (000124)

The mixture of podophyllotoxin (10 mg, 0.024 mmol), 3-chloroacetamidobenzoic acid (12.5 mg, 0.05 mmol), EDCI (25 mg, 0.13 mmol), DMAP (2 mg, 0.02 mmol) and dichloromethane (3 ml) were stirred at room temperature for 22 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting liquid was separated by column chromatography (eluent: ethyl acetate and petroleum ether) to afford 6 mg podophyllotoxin-4-O—[3-chloroacetamidobenzoate], mp.

The chemical structure analysis was performed by $^1$HNMR (CDCl$_3$, 600 MHz): δ 8.36 (s, 1H, Ar—H), 8.17 (s, 1H, Ar—H), 7.90 (d, 2H, Ar—H), 7.55 (s, 1H, Ar—H), 6.86 (s, 1H, Ar—H), 6.59 (s, 1H, Ar—H), 6.45 (s, 2H, Ar—H), 6.14 (s, 1H), 6.00 (s, 2H, OCH$_2$O), 4.65 (s, 1H, H4), 4.44 (s, 1H, H11), 4.31 (t, 1H, H11), 4.21 (s, 2H, ClCH$_2$CO), 3.79 (s, 9H, OCH$_3$), 3.00 (s, 2H, H2,3).

B. 4'-demethylepipodophyllotoxin-4-O-ester of 3-chloroacetamidobenzoic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 3-chloroacetamidobenzoic acid The compound prepared in part B of this Example is converted to the corresponding 4'-phosphate ester as follows: A suspension of 50% NaH in mineral oil and the 4'-demethyl-epipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 12

A. Podophyllotoxin-4-O-ester of chromone-2-carboxylic acid (000215)

The mixture of podophyllotoxin (20 mg, 0.048 mmol), chromone-2-carboxylic acid (19 mg, 0.1 mmol), EDCI (25 mg, 0.13 mmol), DMAP (2 mg, 0.02 mmol) and dichloromethane (3 ml) were stirred at room temperature for 15 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 10 mg podophyllotoxin-4-O-chromone-2-carboxylate, mp.

The chemical structure analysis was performed by $^1$HNMR (CDCl$_3$, 600 MHz): δ 8.22 (s, 1H, Ar—H), 7.78 (s, 1H, Ar—H), 7.58 (s, 1H, Ar—H), 7.49 (s, 1H, Ar—H), 7.15 (s, 1H, Ar—H), 6.83 (s, 1H, Ar—H), 6.61 (s, 1H, Ar—H), 6.42 (s, 2H, Ar—H), 6.15 (s, 1H), 6.03 (s, 2H, OCH$_2$O), 4.67 (s, 1H,), 4.49 (s, 1H, H4), 4.33 (t, 1H, H11), 4.20 (t, 1H, H11), 3.79 (s, 9H, OCH$_3$), 3.02 (s, 2H, H2, 3).

B. 4'-demethylepipodophyllotoxin-4-O-ester of chromone-2-carboxylic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of chromone-2-carboxylic acid The compound prepared in part B of this Example is converted to the corresponding 4'-phosphate ester as follows: A suspension of 50% NaH in mineral oil and the 4'-demethyl-epipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 13

A. Podophyllotoxin-4-O-ester of 5-nitro-2-furoic acid (000202)

The mixture of podophyllotoxin (20 mg, 0.048 mmol), 5-nitro-2-furoic acid (30 mg, 0.2 mmol), EDCI (38 mg, 0.2 mmol), DMAP (2 mg, 0.02 mmol) and dichloromethane (3 ml) were stirred at room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 18.2 mg podophyllotoxin-4-O-[5-nitro-s-furoate], mp.

The chemical structure analysis was performed by $^1$HNMR (CDCl$_3$, 600 MHz); δ 7.38 (s, 2H, Ar—H), 6.81 (s, 1H, Ar—H), 6.61 (s, 1H, Ar—H), 6.48 (s, 2H, Ar—H), 6.19

(d, 1H), 6.01 (t, 2H, OCH$_2$O) 4.65 (s, 1H,), 4.45 (t, 1H, H4), 4.33 (t, 1H, H11), 3.80 (s, 9H, OCH$_3$), 3.01 (m, 2H, H2,3).

B. 4'-demethylepipodophyllotoxin-4-O-ester of 5-nitro-2-furoic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 5-nitro-2-furoic acid The compound prepared in part B of this Example is converted to the corresponding 4'-phosphate ester as follows: A suspension of 50% NaH in mineral oil and the 4'-demethyl-epipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 14

A. Podophyllotoxin-4-O-ester of anthraquinone-2-carboxylic acid (000121)

The mixture of podophyllotoxin (20 mg, 0.048 mmol, anthraquinone-2-carboxylic chloride (27 mg, 0.1 mmol), triethylamine (10 mg, 0.1 mmol), and dichloromethane (3 ml) were stirred at room temperature for 20 h, then dichlormethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 18.2 mg podophyllotoxin-4-O-anthraquinone-2-carboxylate, mp.

The chemical structure analysis was performed by $^1$HNMR (CDCl$_3$, 600 MHz): δ 8.93 (s, 1H, Ar—H), 8.46 (s, 2H, Ar—H), 8.35 (d, 2H, Ar—H), 7.87 (s, 2H, Ar—H), 6.87 (s, 1H, Ar—H), 6.62 (s, 1H, Ar—H), 6.48 (s, 2H, Ar—H), 6.23 (d, 1H), 6.01 (d, 2H, OCH$_2$O), 4.68 (s, 1H,) 4.45 (t, 1H, H4), 4.33 (t, 1H, H11), 3.82 (s, 9H, OCH$_3$), 3.04 (m, 2H, H2, 3).

B. 4'-demethylepipodophyllotoxin-4-O-ester of anthraquinone-2-carboxylic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of anthraquinone-2-carboxylic acid The compound prepared in part B of this Example is converted to the corresponding 4'-phosphate ester as follows: A suspension of 50% NaH in mineral oil and the 4'-demethyl-epipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 15

A. Podophyllotoxin-4-O-ester of 2-phenyl-4-quinolinecarboxylic acid (000125)

The mixture of podophyllotoxin (20 mg, 0.048 mmol), 2-phenyl-4-quinolinecarboxylic acid (12.5 mg, 0.2 mmol), EDCI (25 mg, 0.13 mmol), DMAP (2 mg, 0.02 mmol) and dichloromethane (3 ml) were stirred at room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 18 mg podophyllotoxin-4-O—[2-phenyl-4-quinolinecarboxylate], mp.

The chemical structure analysis was performed by $^1$HNMR (CDCl$_3$, 600 MHz): δ 8.78 (d, 1H, Ar—H), 8.40 (s, 1H, Ar—H), 8.28 (d, 1H, Ar—H), 8.14 (d, 2H, Ar—H), 7.81 (t, 1H, Ar—H), 7.64 (t, 1H, Ar—H), 7.56 (m, 3H, Ar—H), 6.92 (s, 1H, Ar—H), 6.61 (s, 1H, Ar—H), 6.47 (s, 2H, Ar—H), 6.31 (d, 1H), 5.99 (t, 2H, OCH$_2$O), 4.69 (s, 1H,), 4.60 (t, 1H, H4), 4.40 (t, 1H, H11), 3.81 (s, 3H, OCH$_3$), 3.74 (s, 6H, OCH$_3$), 3.07 (m, 2H, H2, 3).

B. 4'-demethylepipodophyllotoxin-4-O-ester of 2-phenyl-4-quinolinecarboxylic acid By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 2-phenyl-4-quinolinecarboxylic acid The compound prepared in part B of this Example is converted to the corresponding 4'-phosphate ester as follows: A suspension of 50% NaH in mineral oil and the 4'-demethyl-epipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 16

A. Podophyllotoxin-4-O-ester of thymine-1-acetic acid (0003061)

The mixture of podophyllotoxin (20 mg, 0.048 mmol), thymine-1-acetic acid (18 mg, 0.1 mmol), EDCI (25 mg, 0.13 mmol), DMAP (2 mg, 0.02 mmol), DMF (2 ml) and dichloromethane (2 ml) were stirred at room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting liquid was separated by column chromatography (eluent: ethyl acetate and petroleum ether) to afford 18 mg podophyllotoxin-4-O—[thymine-1-acetate], mp.

The chemical structure analysis was performed by $^1$HNMR ($CDCl_3$, 600 MHz): δ 9.22 (s, 1H, NH), 7.02 (s, 1H, Ar—H), 6.79 (s, 1H, Ar—H), 6.54 (s, 1H, Ar—H), 6.36 (s, 1H, Ar—H), 6.01 (s, 2H, Ar—H), 5.99 (t, 3H, $OCH_2O$), 4.60 (s, 1H, H4), 4.52 (q, 2H, $COCH_2N$), 4.40 (t, 1H, H11), 4.20 (t, 1H), 3.81 (s, 3H, $OCH_3$), 3.74 (s, 6H, $OCH_3$), 3.07 (m, 2H, H2,3), 1.93 (s, 3H, Ar—H).

B. 4'-demethylepipodophyllotoxin-4-O-ester of thymine-1-acetic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of thymine-1-acetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 17

A. Podophyllotoxin-4-O-ester of hemisuccinic acid (000201)

The mixture of podophyllotoxin (50 mg, 0.12 mmol), succinic anhydride (33 mg, 0.3 mmol), DMAP (2 mg, 0.02 mmol) and THF (3 ml) were stirred at 70° C. for 20 h, then THF was removed and dichloromethane (20 ml) was added to the residue. Organic layer was washed with water (20 ml) and brine (20 ml), and then dried over $MgSO_4$. After the solvent was removed under reduced pressure, the resulting liquid was separated by column chromatography (eluent: ethyl acetate and petroleum ether) to afford 20 mg podophyllotoxin-4-O-hemisuccinate, mp.

The chemical structure analysis was performed by $^1$HNMR ($CDCl_3$, 600 MHz): δ 6.78 (s, 1H, Ar—H), 6.53 (s, 1H, Ar—H), 6.39 (s, 2H, Ar—H), 5.98 (t, 2H, $OCH_2O$), 5.92 (d, 1H), 4.60 (s, 1H, H4), 4.40 (t, 1H, H11), 4.17 (t, 1H), 3.81 (s, 3H, $OCH_3$), 3.76 (s, 6H, $OCH_3$), 2.95 (m, 2H, H2, 3), 2.73 (m, 4H, $COCH_2CH_2CO$).

B. 4'-demethylepipodophyllotoxin-4-O-ester of hemisuccinic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of hemisuccinic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 18

A. Bis(Podophyllotoxin-4-O-ester) of 5-nitroisophthalic acid (000331)

The mixture of podophyllotoxin (30 mg, 0.072 mmol), 5-nitroisophthalic acid (7.6 mg, 0.036 mmol), EDCI (25 mg, 0.13 mmol), DMAP (2 mg, 0.02 mmol) and dichloromethane (3 ml) were stirred at room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 15 mg Bis(Podophyllotoxin-4-O-ester) of 5-nitroisophthalic acid mp.

The chemical structure analysis was performed by $^1$HNMR (CDCl$_3$, 600 MHz): δ 9.03 (s, 2H, Ar—H), 6.79 (s, 2H, Ar—H), 6.63 (s, 2H, Ar—H), 6.46 (s, 4H, Ar—H), 6.25 (d, 1H), 6.02 (s, 2H, OCH$_2$O), 4.69 (s, 1H,), 4.43 (t, 1H, H11), 4.32 (s, 1H,), 3.81 (s, 9H, OCH$_3$), 3.04 (m, 2H, H2,3).

B. 4'-demethylepipodophyllotoxin-4-O-ester of 5-nitroisophthalic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of 5-nitroisophthalic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 19

A. Podophyllotoxin-4-O-ester of N-(tert-Butoxycarbonyl)-L-proline [000203]

The mixture of podophyllotoxin (20 mg, 0.05 mmol), N-(tert-Butoxycarbonyl)-L-proline carboxylic acid (21.5 mg, 0.1 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 3.5 mg Podophyllotoxin-4-O-ester of N-(tert-Butoxycarbonyl)-L-proline carboxylic acid.

The chemical structure analysis was performed by $^1$HNMR (CDCl$_3$, 600 MHz):

B. 4'-demethylepipodophyllotoxin-4-O-ester of N-(tert-Butoxycarbonyl)-L-proline

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of N-(tert-Butoxycarbonyl)-L-proline The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 20

A. Podophyllotoxin-4-O-ester of (+)-menthoxyethanoic acid [000218]

The mixture of podophyllotoxin (20 mg, 0.048 mmol), (+)-menthoxyethanoic acid (20.5 mg, 0.1 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 12 mg Podophyllotoxin-4-O-ester of (+)-menthoxyethanoic acid.

The chemical structure analysis was performed by $^1$HNMR (CDCl$_3$, 600 MHz):

B. 4'-demethylepipodophyllotoxin-4-O-ester of (+)-menthoxyethanoic acid

By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of (+)-menthoxyethanoic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 21

A. Podophyllotoxin-4-O-ester of (+)-2-(2,4,5,7-tetranitro-9-enylideaminooxy)-propionic acid [000222]

The mixture of podophyllotoxin (20 mg, 0.048 mmol), (+)-2-(2,4,5,7-tetranitro-9-enylideaminooxy)-propionic acid (22 mg, 0.048 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting liquid was separated by column chromatography (eluent: ethyl acetate and petroleum ether) to afford Podophyllotoxin-4-O-ester of (+)-2-(2,4,5,7-tetranitro-9-enylideaminooxy)-propionic acid.

The chemical structure analysis was performed by $^1$HNMR ($CDCl_3$, 600 MHz):

B. 4'-demethylepipodophyllotoxin-4-O-ester of (+)-2-(2,4,5,7-tetranitro-9-enylideaminooxy)-propionic acid By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of (+)-2-(2,4,5,7-tetranitro-9-enylideaminooxy)-propionic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 22

A. Podophyllotoxin-4-O-ester of N—BOC-1,2,3,4-Tetrahydro-β-carboline-3-carboxylic acid [000301]

The mixture of podophyllotoxin (20 mg, 0.048 mmol), N—BOC-1,2,3,4-Tetrahydro-β-carboline-3-carboxylic acid (22 mg, 0.07 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting liquid was separated by column chromatography (eluent: ethyl acetate and petroleum ether) to afford 18 mg Podophyllotoxin-4-O-ester of N—BOC-1,2,3,4-Tetrahydro-β-carboline-3-carboxylic acid The chemical structure analysis was performed by $^1$HNMR ($CDCl_3$, 600 MHz):

B. 4'-demethylepipodophyllotoxin-4-O-ester of N—BOC-1,2,3,4-Tetrahydro-β-carboline-3-carboxylic acid By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of N—BOC-1,2,3,4-Tetrahydro-β-carboline-3-carboxylic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N $NH_4OH$ at 50° C. The suspension is filtered, washed with water and concentrated at reduced pressure at 50° C. The solution is then filtered and acidified with HCl to give the title compound.

Example 23

A. Podophyllotoxin-4-O-ester of N—BOC-1,2,3,4-Tetrahydroisoquinoline-3-carboxylic acid [000302]

The mixture of podophyllotoxin (20 mg, 0.048 mmol), N—BOC-1,2,3,4-Tetrahydroisoquinoline-3-carboxylic acid (22 mg, 0.07 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 15 mgPodophyllotoxin-4-O-ester of N—BOC-1,2,3,4-Tetrahydroisoquinoline-3-carboxylic acid.

The chemical structure analysis was performed by $^1$HNMR (CDCl$_3$, 600 MHz):

B. 4'-demethylepipodophyllotoxin-4-O-ester of 4 N—BOC-1,2,3,4-Tetrahydroisoquinoline-3-carboxylic acid By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of N—BOC-1,2,3,4-Tetrahydroisoquinoline-3-carboxylic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 24

A. Podophyllotoxin-4-O-ester of N—BOC-erythro-D-β-Menthylphenylalanine [000307]

The mixture of podophyllotoxin (20 mg, 0.048 mmol), N—BOC-erythro-D-β-Menthylphenylalanine (28 mg, 0.096 mmol), EDCI (25 mg, 0.13 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 23 mg Podophyllotoxin-4-O-ester of N—BOC-erythro-D-β-Menthylphenylalanine The chemical structure analysis was performed by $^1$HNMR (CDCl$_3$, 600 MHz):

B. 4'-demethylepipodophyllotoxin-4-O-ester of N—BOC-erythro-D-β-Menthylphenylalanine By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of N—BOC-erythro-D-β-Menthylphenylalanine The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 25

A. Podophyllotoxin-4-O-ester of camptothecin-20-O-ester of 4-carboxylicphenoxyacetic acid [000801]

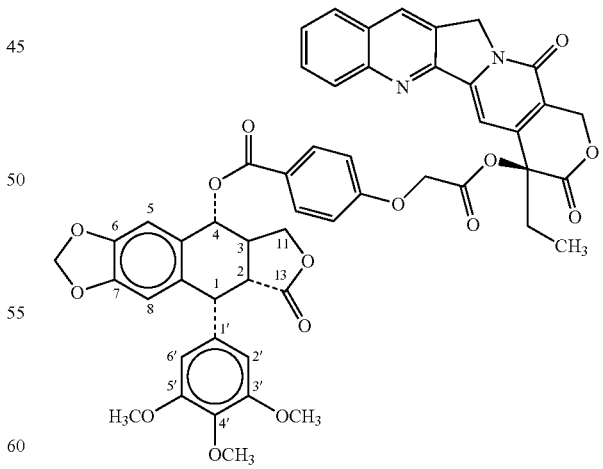

The mixture of podophyllotoxin (30 mg, 0.072 mmol), camptothecin-20-O-ester of 4-carboxylicphenoxyacetic acid (15 mg, 0.028 mmol—see U.S. Pat. No. 6,350,756), EDCI (20 mg, 0.10 mmol), DMAP (2 mg, 0.02 mmol) and dichloromethane (3 ml) were stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting liquid was separated by column chromatography (eluent: ethyl acetate and petroleum ether) to afford 5.0 mg Podophyllotoxin-4-O-ester of camptothecin-20-O-ester of 4-carboxylicphenoxyacetic acid.

The chemical structure analysis was performed by $^1$HNMR (CDCl$_3$, 600 MHz):

B. 4'-demethylepipodophyllotoxin-4-O-ester of camptothecin-20-O-ester of 4-carboxylicphenoxyacetic acid By following the procedure of Part A of this Example, but substituting 4'-demethylepipodophyllotoxin for podophyllotoxin, one obtains the corresponding 4'-demethylepipodophyllotoxin compound.

C. 4'-Phosphate ester of 4'-demethylepipodophyllotoxin-4-O-ester of camptothecin-20-O-ester of 4-carboxylicphenoxyacetic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

D. Podophyllotoxin-4-O-ester of camptothecin derivative-20-O-ester of 4-carboxylicphenoxyacetic acid By following the methods described above and substituting camptothecin with a camptothecin derivative disclosed in U.S. Pat. No. 6,350,756, those skilled in the art will be able to prepare a compound of this invention analogous to compounds described in A, B, and C of this example, which has a 20-O-ester of a camptothecin derivative.

Example 26

A. Bis(Podophyllotoxin-4-O-ester) of 3,5-Pyridinedicarboxylic acid [000330]

The mixture of podophyllotoxin (36 mg, 0.072 mmol), 3,5-Pyridinedicarboxylic acid (10 mg, 0.036 mmol), EDCI (25 mg, 0.13 mmol), DMAP (2 mg, 0.02 mmol) and dichloromethane (3 ml) were stirred in the room temperature for 20 h, then dichloromethane was added to the solution. Organic layer was washed with water, saturated NaHCO$_3$ aqueous solution and brine, and then dried over MgSO$_4$. After the solvent was removed under reduced pressure, the resulting liquid was separated by column chromatography (eluent: ethyl acetate and petroleum ether) to afford 20 mg of bis (podophyllotoxin-4-O-ester of 3,5-pyridinedicarboxylic acid.

The chemical structure analysis was performed by $^1$HNMR (CDCl$_3$, 600 MHz):

B. Bis(4'-demethylepipodophyllotoxin-4-O-ester) of 3,5-Pyridinedicarboxylic acid By following the procedure of Part A of this Example, but substituting 4'-demethylepipodophyllotoxin for podophyllotoxin, one obtains the corresponding 4'-demethylepipodophyllotoxin compound.

C. Bis(4'-Phosphate ester of 4'-demethylepipodophyllotoxin-4-O-ester) of 3,5-Pyridinedicarboxylic acid The compound prepared in part B of this Example is converted to the corresponding 4'-phosphate ester as follows: A suspension of 50% NaH in mineral oil and the 4'-demethylepipodophyllotoxin-4-O-ester of Part B of this Example in DMF is stirred for 30 minutes at room temperature. After the mixture is cooled to 0° C., a solution of dibenzylphosphorochloridate in toluene is added drop by drop. The solution is stirred at room temperature for 15 minutes and then diluted with cold water and extracted with ether. The ether solution is washed with water, dried, evaporated under reduced pressure to give the 4'-dibenzylphosphate derivative of the compound of part B. A solution of the dibenzylphosphate derivative in 85% ethanol is hydrogenated in a Parr apparatus in the presence of 10% Pd supported on carbon. After theoretical absorption of hydrogen, the catalyst is filtered, washed with cold water and suspended in 2N NH$_4$OH at 50° C. The suspension is filtered, washed with water and concentrated at reduced pressure at 50° C. The solution is then filtered and acidified with HCl to give the title compound.

Example 27

This example provides directions for growing cells and testing compounds of the invention for their effect on the growth of the cells. All cells were purchased from DCTDC Tumor Repository, NCI, NIH.

Cell Colony Formation Assay

Four hundred cells (HCT 116, PC-3) or five hundred cells (VM46) were plated in 60 mm Petri dishes containing 2.7 ml of medium (modified McCoy's 5a medium) containing 10% fetal bovine serum and 100 units/ml penicillin and 100 mg/ml streptomycin. The cells were incubated in a CO$_2$ incubator at 37° C. for 5 hours for attachment to the bottom of Petri dishes. Drugs were made fresh in medium at ten times the final concentration, and then 0.3 ml of this stock solution was added to the 2.7 ml of medium in the dish. The cells were then incubated with drugs for 72 hours at 37° C. At the end of the incubation the drug-containing media were decanted, the dishes were rinsed with 4 ml of Hank's Balance Salt Solution (HBSS), 5 ml of fresh medium was added, and the dishes were returned to the incubator for colony formation. The cell colonies were counted using colony counter after incubation for 7 days for HCT116 cells and PC-3 cells and 8 days for VM46 cells, respectively. Cell survival (%) was calculated, as shown in Table I below for HCT 116 cells.

Values of ID50 (the drug concentration producing 50% inhibition of colony formation) may be determined for each tested compound. The directions described in this example may be used in other cells, such as DU-145.

The compounds of this invention are administered to C3H/HeJ mice by intraperitoneal injection. Drug toxicity is evalu-

TABLE I

This table provides results of in vitro efficacy tests performed in example 16 for the cell line HCT116.

| | In Vitro Efficacy: Survival (%) of HCT116 | | | | In Vivo Toxicity nontoxic dose (ip, mg/kg) in | In Vivo Efficacy | |
|---|---|---|---|---|---|---|---|
| | | | | | | Surviving days after treatment of MTG-B mouse mammary adenocarcinoma in | |
| Compounds | 1000 nM | 100 nM | 10 nM | 1 nM | C3H/Hcj mice | C3H/Hej mice | T/C % |
| Etoposide | | | 100 | | | | |
| 000121 | 0 | 94.03 | | | | | |
| 000201 | 0 | 93.24 | | | | | |
| 000125 | 0 | 90.34 | | | | | |
| 000202 | 0 | 0 | 81.68 | | | | |
| 000203 | 0 | 89.76 | | | | | |
| 000124 | 0 | 0 | 83.22 | | | | |
| 000215 | 0 | 0 | 92.46 | | | | |
| 000218 | 0 | 44.28 | | | | | |
| 000222 | 0 | 1.46 | 100 | | | | |
| 000301 | 0 | 84.08 | | | | | |
| 000302 | 0 | 100 | | | | | |
| 0003061 | 0 | 0 | 100 | | 100 (70) | 13 | 217 |
| 000307 | 0 | 93.49 | | | | | |
| 0003132 | 0 | 97.65 | | | | | |
| 000317 | 0 | 0 | 99.49 | | | | |
| 000320 | 0 | 0 | 100 | | | | |
| 000323 | 0 | 0 | 90.86 | | | | |
| 000324 | 0 | 0 | 100 | | | | |
| 000329 | 0 | 0 | 100 | | | | |
| 000330 | 0 | 0 | 100 | | | | |
| 000331 | 0 | 62.56 | | | | | |
| 000405 | 0 | 0 | 90.45 | | | | |
| 000614 | 0 | 0 | 84.99 | | | | |
| 000615 | 0 | 0 | 100 | | | | |
| 000622 | 0 | 0 | 98.48 | | | | |
| 000801 | 0 | 0 | 0 | 99.83 | | | |

Example 28

This example provides directions for performing in vivo toxicity tests of the compounds of the invention on C3H/HeJ mice.

Acute toxicities of the compounds of this invention are evaluated on C3H/HeJ mice (body weight 18-22 g). The MTD40 (maximum tolerated dose at day 40) values are determined by the standard procedure described by Gad and Chengelis (see, for example, "Acute Toxicology Testing," 2nd Ed., Shayne O. Gad and Christopher P. Chengelis, pp. 186-195 (Academic Press).) In the consecutive type studies, 2 mice are dosed at low and moderate doses of 40 and 100 mg/kg. If no severe and irreversible toxicity (euthanasia is required) occurs at these doses, a new pair of animals is initiated at 180 mg/kg, which is 1.8 times higher than 100 mg/kg. Sequential dosages (about 3 doses on 3 pairs of animals, i.e. 2 mice for each drug dose) are increased by a factor of 1.8 until severe and irreversible toxicity (euthanasia is required) occurred. Then another pair of animals is initiated at the highest nonlethal dosage, and successive dosages were increased by a factor of 1.15. The result of this exercise is two dosages, one apparently nonlethal and the other lethal if severe and irreversible toxicity occurs and euthanasia is required, separated by a factor of 1.15. Six mice are dosed at each dosage. If no severe and irreversible toxicity occurs at the lower dosage and at least one with severe and irreversible toxicity occurs at the higher dose, then the lower dose is considered to be the MTD.

ated on mice checked daily for 45 days. The toxicity parameters reported will be the MTD40. The MTD is defined as the highest dose causing no severe irreversible toxicity in one treatment group, but at least one animal exhibiting severe and irreversible toxicity and being euthanized at the next higher dose. The acute toxicity of the podophyllotoxin-4-O-ester of thymine-1-acetic acid (compound 3061, described in Example 16) is shown above in Table 1.

Example 29

This example provides directions for performing in vivo efficacy tests of the compounds of the invention on C3H/HeJ mice bearing MTG-B tumors.

Studies on the compounds of this invention are performed on C3H/HeJ mice bearing MTG-B tumors. The tumors grow exponentially following implantation into the flanks of the mice and reached a diameter of 8 mm (268.08 mm$^3$) by day 7 to 10. Treatment is initiated at that time, with the first day of treatment designated as day 0 for calculation and plots. The mice are injected i.p. with three drug dose levels (⅓, ½, 1×MTD) using both a single injection and the schedule of Q2D×3 (every 2 days for a total of 3 treatments at ⅓ MTD). Control groups of mice bearing 8 mm diameter tumors are treated with vehicle alone. After drug treatment, the mice are observed twice a day. When a tumor reaches 1.5 g, the mouse bearing the tumor is euthanized. Surviving days measured from day 0 for mice treated with anticancer drugs (T) and surviving days measured from day 0 for control mice (C) are recorded. Tumor growth inhibition values (T/C %) are calculated using the formula T/C %=(surviving days of mice treated with an anticancer drug T/surviving days of control mice C)×100%.

Tumor sizes may be measured by caliper every day. Daily measurement (mm) of solid tumor (length L and width W) in two dimensions is used to calculate the tumor weight [tumor weight=(length×width$^2$)/2] based on the interchangeable value of 1 mm$^3$=1 mg. Tumor growth delay (T–C value) is determined by calculation of the median time (in days) required for the treatment group and control group tumors to reach 1,000 mg. Tumor doubling time (Td) is measured, and tumor cell kill is calculated by the formula of log cell kill= (T–C value)/(3.32×Td). Regression effects after treatment may be observed and recorded (a complete regression: a regression below limit of palpation; a partial regression: a regression of more than 50% reduction in tumor mass).

Generally, the survival time of the control mice is six (6) days. A ratio of the extra days of survival of mice treated with the compounds of the invention (compared to control) to the extra days of survival of mice treated with taxol (compared to control), can be calculated. For example, if the mice survived 18 days as compared to 9 days for taxol-treated mice, the CD/Taxol ratio would be 18-6/9-6=12/3=4. The in vivo efficacy of the podophyllotoxin-4-O-ester of thymine-1-acetic acid (compound 3061, described in Example 16) is shown in Table 1 below.

Example 30

This example provides guidance for determining the inhibition of topoisomerase II. This procedure is a modification of a published procedure for the P4 knotted DNA unknotting reaction found at *J. Biol. Chem.* 1983, 258, 8413. A more recent publication can be found at *J. Med. Chem.* 1989, Vol. 32, No. 3 at page 608. A reaction mixture (20 μL), which contains 50 mM HEPES pH 6.7, 50 mM KCl, 100 mM NaCl, 0.1 mM EDTA, 10 mM HgCl$_2$, 0.1 mM ATP, 50 μg/mL bovine serum albumin, 0.26 μg P4 knotted DNA, and enzyme, is incubated with or without a compound of the invention.

The reaction mixture is incubated at 37° C. for 30 min and terminated by adding a stop solution (2% sodium dodecyl sulfate, 20% glycerol, 0.05% bromphenol blue). These samples are loaded onto a 1% agarose gel and electrophoresed at 50 V overnight with an electrophoresis buffer that contains 90 mM Tris-boric acid, pH 8.3, and 2.5 mM EDTA. At completion, the gel is stained in 0.5 μg/mL of ethidium bromide. Then a photograph is taken of the DNA bands visualized with fluorescence induced by a long-wavelength UV lamp. The data is reported.

The subject matter claimed is:

1. A compound represented by the formula:

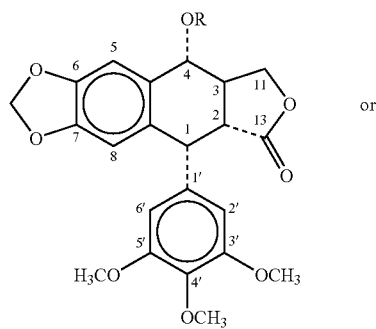

or

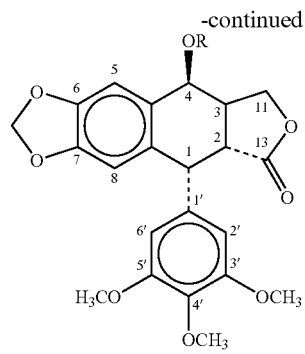

wherein
R is C(O)—R$_1$, and
R$_1$ is

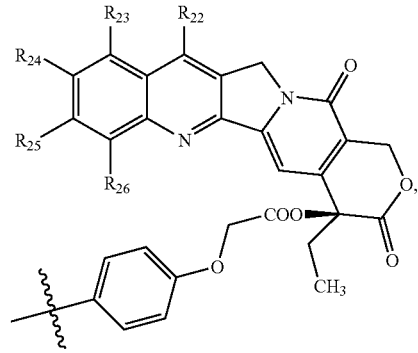

R$_2$ is hydrogen, PO$_3$H$_2$ or PO(OR$_3$)$_2$ where R$_3$ is benzyl;

R$_{22}$ is hydrogen, halo, lower alkyl, lower alkoxy, hydroxy, R$_{40}$C(O)O, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, mono- or di-alkylcarbonyl, alkylcarbonylmethyl, benzoylmethyl, benzylcarbonyloxymethyl, or mono- or di lower alkoxymethyl;

R$_{23}$ is hydrogen, halo, lower alkyl, lower alkoxy, hydroxy, R$_{40}$C(O)O, cyano, nitro, amino, halogenated lower alkyl, halogenated lower alkoxy, hydroxycarbonyl, formyl, lower alkoxycarbonyl, CH$_2$NR$_{27}$R$_{28}$ (where each of R$_{27}$ and R$_{28}$ is independently H—, alkyl of 1-6 carbons, optionally substituted phenyl, hydroxy lower alkyl, amino lower alkyl, or mono- or dialkylamino lower alkyl, or R$_{27}$ and R$_{28}$ taken together with —N— represent a cyclic amino-), CH$_2$R$_{29}$ (where R$_{29}$ is lower alkoxy, CN, amino lower alkoxy, mono- or di-lower alkylamino lower alkoxy, lower alkylthio, amino lower alkylthio, or mono- or di-lower alkylamino lower alkylthio), or NR$_{30}$R$_{31}$ (where each of R$_{30}$ and R$_{31}$ is independently hydrogen, lower alkyl, phenyl, hydroxy lower alkyl, amino lower alkyl, or mono- or di-lower alkyl, or R$_{30}$ and R$_{31}$ taken together with —N— represent a cyclic amino), dialkylamino alkyl, lower alkylcarbonyloxy, or lower alkylcarbonylamino;

R$_{24}$ is hydrogen, halo, lower alkyl, lower alkoxy, hydroxy, R$_{40}$C(O)O, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R_{24}$ together with $R_{25}$ is methylenedioxy;

$R_{25}$ is hydrogen, halo, lower alkyl, lower alkoxy, hydroxy, $R_{40}C(O)O$, cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and $R_{26}$ is hydrogen, halo, lower alkyl, lower alkoxy, hydroxy, $R_{40}C(O)O$, cyano, nitro, amino, halogenated lower alkyl, halogenated lower alkoxy, hydroxycarbonyl, formyl, lower alkoxycarbonyl, lower alkylcarbonyloxy, or lower alkylcarbonylamino;

$R_{40}$ is $R_{41}-O-(CH_2)_s-$;

s is an integer of 1-10;

$R_{41}$ is selected from the group consisting of lower alkyl;

phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino;

cycloalkyl of 3-7 carbons, optionally substituted with one to five substituents independently selected from the group consisting of halo, lower alkyl, lower alkoxy, hydroxy, cyano, nitro, amino, halogenated lower alky, halogenated lower alkoxy, hydroxycarbonyl, lower alkoxycarbonyl, lower alkylcarbonyloxy, and lower alkylcarbonylamino;

a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; and a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

wherein the wavy line represents the point of connection to C(O).

2. The compound of claim 1, wherein $R_{22}$ is hydrogen;

$R_{23}$ is $CH_2NR_{27}R_{28}$ (where each of $R_{27}$ and $R_{28}$ is independently H—, alkyl of 1-6 carbons, optionally substituted phenyl, hydroxy lower alkyl, amino lower alkyl, or mono- or dialkylamino lower alkyl, or $R_{27}$ and $R_{28}$ taken together with —N— represent a cyclic amino-), $NR_{30}R_{31}$ (where each of $R_{30}$ and $R_{31}$ is independently hydrogen, lower alkyl, phenyl, hydroxy lower alkyl, amino lower alkyl, or mono- or di-lower alkyl, or $R_{30}$ and $R_{31}$ taken together with —N— represent a cyclic amino), or dialkylamino alkyl;

$R_{24}$ is selected from the grout consisting of lower alkoxy, hydroxy, halogenated lower alkyl, halogenated lower alkoxy, hydroxycarbonyl, formyl, lower alkoxycarbonyl, carbamoyloxy, and lower alkylcarbonyloxy, or $R_{24}$ together with $R_{25}$ is methylenedioxy;

$R_{25}$ is hydrogen, or together with $R_{24}$ is methylenedioxy;

$R_{26}$ is hydrogen.

3. The compound of claim 2, wherein $R_{23}$ is $CH_2NR_{27}R_{28}$ (where each of $R_{27}$ and $R_{28}$ is lower alkyl), $R_{25}$ is hydrogen, and $R_{24}$ is hydroxy, alkoxy or alkylcarbonyloxy.

4. The compound of claim 3, wherein $R_{23}$ is $CH_2N(CH_3)_2$ and $R_{24}$ is hydroxy.

5. The compound of claim 1, wherein $R_{22}$ is hydrogen, lower alkyl, or halogenated lower alkyl;

$R_{23}$ is hydrogen or lower alkyl;

$R_{24}$ is selected from the group consisting of lower alkoxy, hydroxy, halogenated lower alkoxy, carbamoyloxy, and lower alkylcarbonyloxy, or $R_{24}$ together with $R_{25}$ is methylenedioxy;

$R_{25}$ is hydrogen, or together with $R_{24}$ is methylenedioxy; and $R_{26}$ is hydrogen.

6. The compound of claim 5, wherein $R_{23}$ is hydrogen, $R_{25}$ is hydrogen, and $R_{24}$ is carbamoyloxy.

7. The compound of claim 5, wherein $R_{22}$ is lower alkyl and $R_{24}$ is 4-(1-piperidino)-1-piperidinocarbonyloxy.

8. The compound of claim 7, wherein $R_{22}$ is ethyl.

9. The compound of claim 1, wherein $R_{22}$ is lower alkyl;

$R_{23}$ is hydrogen;

$R_{24}$ is selected from the group consisting of hydroxy, lower alkoxy, halogenated lower alkoxy, hydroxycarbonyl, formyl, lower alkoxycarbonyl, carbamoyloxy, and lower alkylcarbonyloxy;

$R_{25}$ is hydrogen; and $R_{26}$ is hydrogen.

10. The compound of claim 9, wherein $R_{22}$ is ethyl and $R_{24}$ is hydroxy.

11. The compound of claim 1, wherein each of $R_{22}$, $R_{24}$, $R_{25}$, and $R_{26}$ is hydrogen; and $R_{23}$ is amino or nitro.

12. The compound of claim 11, wherein $R_{23}$ is amino.

13. The compound of claim 12, wherein $R_{23}$ is nitro.

14. The compound of claim 1, wherein $R_{22}$ is tri-lower alkylsilyl;

$R_{23}$ is hydrogen;

$R_{24}$ is selected from the group consisting of hydroxy, lower alkoxy, halogenated lower alkoxy, hydroxycarbonyl, formyl, lower alkoxycarbonyl, carbamoyloxy, and lower alkylcarbonyloxy;

$R_{25}$ is hydrogen; and $R_{26}$ is hydrogen.

15. The compound of claim 14, wherein $R_{22}$ is t-butyldimethylsilyl and $R_{24}$ is hydroxy.

16. A compound of claim 1, selected from:

[structure]

[structure]

[structure]

[-continued structure]

or a pharmaceutically acceptable salt thereof

17. A compound of claim 1 represented by the formula:

[structure]

wherein
R is C(O)—R$_1$, and
R$_1$ is

[structure]

R$_{22}$ is hydrogen, halo, lower alkyl, lower alkoxy, hydroxy, R$_{40}$C(O)O, cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, mono- or di-alkylcarbonyl, alkylcarbonylmethyl, benzoylmethyl, benzylcarbonyloxymethyl, or mono- or di lower alkoxymethyl;

$R_{23}$ is hydrogen, halo, lower alkyl, lower alkoxy, hydroxy, $R_{40}C(O)O$, cyano, nitro, amino, halogenated lower alkyl, halogenated lower alkoxy, hydroxycarbonyl, formyl, lower alkoxycarbonyl, $CH_2NR_{27}R_{28}$ (where each of $R_{27}$ and $R_{28}$ is independently H—, alkyl of 1-6 carbons, optionally substituted phenyl, hydroxy lower alkyl, amino lower alkyl, or mono- or dialkylamino lower alkyl, or $R_{27}$ and $R_{28}$ taken together with —N— represent a cyclic amino-), $CH_2R_{29}$ (where $R_{29}$ is lower alkoxy, CN, amino lower alkoxy, mono- or di-lower alkylamino lower alkoxy, lower alkylthio, amino lower alkylthio, or mono- or di- lower alkylamino lower alkylthio), or $NR_{30}R_{31}$ (where each of $R_{30}$ and $R_{31}$ is independently hydrogen, lower alkyl, phenyl, hydroxy lower alkyl, amino lower alkyl, or mono- or di-lower alkyl, or $R_{30}$ and $R_{31}$ taken together with —N— represent a cyclic amino), dialkylamino alkyl, lower alkylcarbonyloxy, or lower alkylcarbonylamino;

$R_{24}$ is hydrogen, halo, lower alkyl, lower alkoxy, hydroxy, $R_{40}C(O)O$, cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R_{24}$ together with $R_{25}$ is methylenedioxy;

$R_{25}$ is hydrogen, halo, lower alkyl, lower alkoxy, hydroxy, $R_{40}C(O)O$, cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and $R_{26}$ is hydrogen, halo, lower alkyl, lower alkoxy, hydroxy, $R_{40}C(O)O$, cyano, nitro, amino, halogenated lower alkyl, halogenated lower alkoxy, hydroxycarbonyl, formyl, lower alkoxycarbonyl, lower alkylcarbonyloxy, or lower alkylcarbonylamino;

$R_{40}$ is $R_{41}-O-(CH_2)_s-$;

s is an integer of 1-10;

$R_{41}$ is selected from the group consisting of:

lower alkyl;

phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino;

cycloalkyl of 3-7 carbons, optionally substituted with one to five substituents independently selected from the group consisting of halo, lower alkyl, lower alkoxy, hydroxy, cyano, nitro, amino, halogenated lower alky,
halogenated lower alkoxy, hydroxycarbonyl, lower alkoxycarbonyl, lower alkylcarbonyloxy, and lower alkylcarbonylamino;

a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; and a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

wherein the wavy line represents the point of connection to C(O).

18. A compound of claim 17, which compound is:

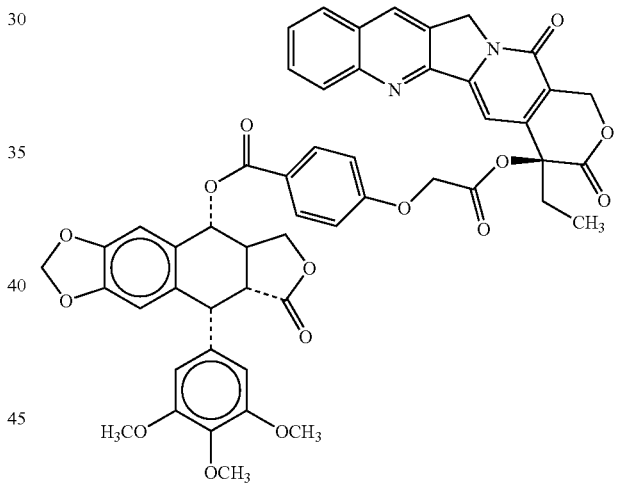

or a pharmaceutically acceptable salt thereof.

19. The compound of any one of claims 1-16, 17 and 18 in combination with a pharmaceutically-acceptable excipient to form a pharmaceutical composition.

20. The pharmaceutical composition of claim 19, which is in the form of a liposomal composition.

* * * * *

UNITED STATES PATENT AND TRADEMARK OFFICE
CERTIFICATE OF CORRECTION

PATENT NO. : 7,605,262 B2  
APPLICATION NO. : 12/016926  
DATED : October 20, 2009  
INVENTOR(S) : Li-Xi Yang Page 1 of 1

It is certified that error appears in the above-identified patent and that said Letters Patent is hereby corrected as shown below:

Claims

In claim 1, Column 48, beginning at Line 2, please delete

" 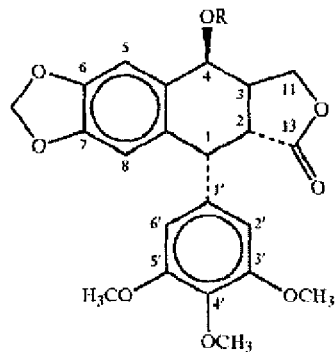 " and replace with 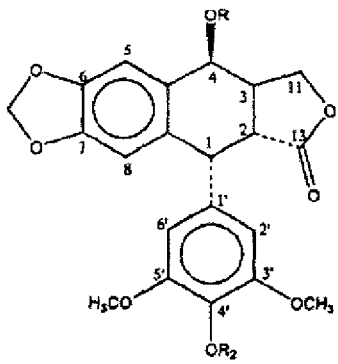 .

Signed and Sealed this  
First Day of March, 2016

Michelle K. Lee  
*Director of the United States Patent and Trademark Office*